US010251958B2

(12) United States Patent
Stenzel et al.

(10) Patent No.: US 10,251,958 B2
(45) Date of Patent: Apr. 9, 2019

(54) NANOPARTICLES FOR DRUG DELIVERY COMPRISING ALBUMIN HAVING A POLYMER CHAIN COUPLED THERETO

(71) Applicant: NEWSOUTH INNOVATIONS PTY LIMITED

(72) Inventors: Martina Heide Stenzel, Malabar (AU); Wei Scarano, East Hills (AU); Domenic Svejkar, Reandwich (AU); Mingtao Liang, Cameron Park (AU)

(73) Assignee: NEWSOUTH INNOVATIONS PTY LIMITED, Sydney (AU)

( * ) Notice: Subject to any disclaimer, the term of this patent is extended or adjusted under 35 U.S.C. 154(b) by 0 days.

(21) Appl. No.: 14/782,042

(22) PCT Filed: Apr. 1, 2014

(86) PCT No.: PCT/AU2014/000346
§ 371 (c)(1),
(2) Date: Oct. 2, 2015

(87) PCT Pub. No.: WO2014/161031
PCT Pub. Date: Oct. 9, 2014

(65) Prior Publication Data
US 2016/0074530 A1 Mar. 17, 2016

(30) Foreign Application Priority Data
Apr. 2, 2013 (AU) ................. 2013901119

(51) Int. Cl.
| | |
|---|---|
| *A61K 47/64* | (2017.01) |
| *A61K 47/69* | (2017.01) |
| *A61K 47/48* | (2006.01) |
| *A61K 47/42* | (2017.01) |
| *A61K 9/14* | (2006.01) |
| *A61K 31/12* | (2006.01) |
| *A61K 47/32* | (2006.01) |
| *A61K 9/107* | (2006.01) |
| *A61K 31/282* | (2006.01) |
| *A61K 31/713* | (2006.01) |
| *A61K 47/60* | (2017.01) |
| *A61K 47/58* | (2017.01) |
| *A61K 47/59* | (2017.01) |

(52) U.S. Cl.
CPC ...... *A61K 47/48869* (2013.01); *A61K 9/1075* (2013.01); *A61K 9/141* (2013.01); *A61K 31/12* (2013.01); *A61K 31/282* (2013.01); *A61K 31/713* (2013.01); *A61K 47/32* (2013.01); *A61K 47/42* (2013.01); *A61K 47/58* (2017.08); *A61K 47/593* (2017.08); *A61K 47/60* (2017.08); *A61K 47/643* (2017.08); *A61K 47/6925* (2017.08)

(58) Field of Classification Search
CPC .. A61K 9/141; A61K 31/12; A61K 47/48176; A61K 9/1075; A61K 47/482

USPC ............. 424/491; 514/44 A, 492, 679
See application file for complete search history.

(56) References Cited

U.S. PATENT DOCUMENTS

2007/0276088 A1* 11/2007 Maynard .......... A61K 47/48176
525/54.1

OTHER PUBLICATIONS

FDA Guideline, title: Guideline for determination of residual moisture in dried biological product; prepared by Center for biologics evaluation and research, published Jan. 1990.*
De et al, title:Temperature-Regulated Activity of Responsive Polymer-Protein Conjugates Prepared by Grafting-from via RAFT Polymerization; J. Am. Chem. Soc., 2008, 130 (34), pp. 11288-11289, Publication Date (Web): Jul. 30, 2008.*
Gregory N., et al.; title: Trapping of Thiol-Terminated Acrylate Polymers with Divinyl Sulfone to Generate Well-Defined Semitelechelic Michael Acceptor Polymers; Macromolecules 2009, 42, 7657-7663, Published on Web Oct. 1, 2009.*
Ulf Nobbmann; title: Polydispersity—what does it mean for DLS and chromatography? Published Oct. 23, 2014. Downloaded from http://www.materials-talks.com/blog/2014/10/23/polydispersity-what-does-it-mean-for-dls-and-chromatography/ on Jun. 21, 2017.*
Metrohm; title: Analysis of residual moisture in a lyophilized pharmaceutical product by near-infrared spectroscopy. Downloaded from file:///C:/Users/yzhang1/Downloads/1276207_AB-358_1_EN%20(1).pdf on May 10, 2018. (Year: 2018).*
Neil P. Desai, title: The nab®Platform : Platform : From Bench to the Clinic and Beyond From Bench to the Clinic and Beyond; Jul. 12-13, 2010. (Year: 2010).*
International Search Report issued by the International Searching Authority on May 15, 2014 for international application PCT/AU2014/000346, filed on Apr. 1, 2014 and published as WO 2014/161031 on Sep. 10, 2014 (Applicant—NewSouth Innovations Pty Limited // Inventor—Stenzel, et al.) (4 pages).
Boyer, C. et al., "An overview of protein-polymer particles", Soft Matter (2011) vol. 7, pp. 1599 to 1614.
Ge, J. et al., "Protein-Polymer Hybrid Nanoparticles for Drug Delivery", Small (2012) vol. 8 No. 23, pp. 3573 to 3578.
Ge, J. et al., "Bovine Serum Albumin-Poly (methyl methacrylate) Nanoparticles: An Example of Frustrated Phase Separation" Nano Letters (2011) vol. 11 No. 6, pp. 2551 to 2554.

(Continued)

*Primary Examiner* — Yanzhi Zhang
(74) *Attorney, Agent, or Firm* — Ballard Spahr LLP

(57) ABSTRACT

The invention provides a dispersion of assemblies. The assemblies comprise an albumin derivative comprising albumin having a polymer chain coupled thereto, wherein the assemblies comprise a core comprising the polymer chains and a shell comprising the albumin. A process for making the dispersion and methods of using the dispersion are also described.

15 Claims, 22 Drawing Sheets

(56) References Cited

OTHER PUBLICATIONS

Li, M. et al., "Responsive Polymer-Protein Bioconjugates Prepared by RAFT Polymerization and Copper-Catalyzed Azide-Alkyne Click Chemistry", Abstracts of Papers, 235th ACS National Meeting Apr. 6-10, Macromol. Rapid Commun. (2008) vol. 29, pp. 1172-1176.
Database Chemical Abstracts; & Li, M. et al., "Responsive polymer-protein bioconjugates prepared by RAFT polymerization and grafting-to via click chemistry" Abstracts of Papers, 235th ACS National Meeting, Apr. 6, 2008 (1 Page).
Elzoghby, A. O. et al., "Albumin-based nanoparticles as potential controlled release drug delivery systems" Journal of Controlled Release, (2011) 157(2):168-182 (16 pages).
Extended European Search Report dated Mar. 7, 2016 by the European Patent Office for EP Application No. 14778412.8, which was filed on Apr. 1, 2014 and published as EP 2981291 on Feb. 10, 2016 (Applicant—New South Innovations Pty Limited) (7 pages).

\* cited by examiner

RAFT polymerization of DMAEMA

Deprotection of PDMAEMA

NANOPARTICLES FOR DRUG DELIVERY COMPRISING ALBUMIN HAVING A POLYMER CHAIN COUPLED THERETO

CROSS REFERENCE TO RELATED APPLICATIONS

This application is a national phase filing of International Patent Application No. PCT/AU2014/000346, filed Apr. 1, 2014, which claims priority to Australian Patent Application No. 2013901119, filed on Apr. 2, 2013, both of which are herein incorporated by reference in their entireties.

FIELD

The invention relates to albumin containing nanoparticles for use in drug delivery.

BACKGROUND

Albumin, a small protein of about 5 nm diameter, which is in abundance in the blood, has a strong tendency to accumulate in tumors. Albumin has therefore been used as drug carrier, since it has a hydrophobic pocket that can encapsulate hydrophobic drugs.

Loading of a drug into albumin can occasionally be achieved by mixing the drug and carrier although this is often not the most promising approach. More commonly, the drug is conjugated to albumin using established procedures. A prodrug is conjugated to the protein—often via a cleavable peptide linker—using maleimides, isocyanates, N-hydroxysuccinimide esters and others. This approach has been applied to several drugs, among them doxorubicin, 5-fluorouracil and platinum (II).

The EPR (enhanced permeation and retention) effect of tumors however is more pronounced with particles well above the size of a single albumin molecule. Nanoparticles in the range above 20 nm are known to lodge in tumors but cannot readily be cleared from the site, leading to retention of the drug carrier in the tumor. Therefore, albumin has been converted into nano-sized particles via a precipitation process. In this process the drug functions to aggregate the molecules of albumin. As a result several hundred albumin molecules build up a particle with a size of more than 200 nm. The product is commonly known as nab-albumin and a version with paclitaxel has recently been marketed as Abraxane®.

A disadvantage of the nab-albumin technology is that it is not well suited to producing particles below 100 nm in diameter: the nature of the processing step does not favour the formation of smaller particles. However, it is known that for good lodgement in tumors, smaller particles are required. Additionally, the nab-albumin technology is not suitable for the use with a number of useful drugs such as genes, peptides and proteins.

There is therefore a need for an albumin-based product having particle size below 100 nm in diameter and capable of encapsulating a range of different drugs, preferably drugs capable of treating tumors.

SUMMARY OF INVENTION

In a first aspect of the invention there is provided a dispersion of assemblies. The assemblies may be aggregated assemblies. They may be aggregates. They may be self-assembled. The assemblies are assemblies of an albumin derivative comprising albumin having a polymer chain coupled, optionally bonded (e.g. covalently bonded) thereto. The assemblies comprise a core comprising the polymer chains and a shell comprising the albumin.

The following aspects may be used in conjunction with the first aspect, either individually or in any suitable combination.

The polymer chains may be chains that are not polyethyleneglycol chains. The polymer chains may be electrically charged. They may be hydrophobic. In this context the term "hydrophobic" may be taken to indicate that the chains are such that the albumin derivative is amphiphilic so as to allow it to self-assemble in water to form the assemblies. Thus the polymer chains may be such that they are not uncharged hydrophilic chains. In this context, "hydrophilic" may be taken to mean not hydrophobic; i.e. that the albumin derivative is not amphiphilic and that it is unable to form the assemblies in water in the absence of other species to facilitate self-assembly.

The dispersion may additionally comprise a biologically active substance. The biological substance may be located in the assemblies of the dispersion. It may be located at least partially in the core of the assemblies. The biologically active substance may be active in treatment of an inflammation or of a tumor. It may be an anti-cancer agent or anti-cancer drug.

The polymer chain may be electrically charged (either positively or negatively). In this case the biologically active substance (if present) may be a counterion for the electrically charged polymer chains.

The albumin may be bovine serum albumin or human serum albumin.

The polymer chain may be a chain growth polymer or a step growth polymer, e.g. a poly(meth)acrylate, a polylactide, a polypeptide, a hydrophobic polyether or a polyolefin. The polymer chain may have a number average molecular weight of from about 1000 to about 1,0000,000. It may have a polydispersity index of about 1.2 to about 2.

The assemblies may have a mean diameter of less than about 100 nm. They may be substantially monodispersed in diameter.

The assemblies may be crosslinked. They may be crosslinked through the albumin. They may comprise crosslinking units derived from a dialdehyde such as glutaraldehyde.

In an embodiment there is provided a dispersion of substantially monodispersed assemblies having a mean diameter of less than about 100 nm, said assemblies comprising an albumin derivative comprising albumin having a hydrophobic polymer chain coupled thereto, wherein the assemblies comprise a core comprising the polymer chains and a shell comprising the albumin and have an anti-cancer drug located at least partially in the core of the amphiphile assemblies.

In another embodiment there is provided a dispersion of substantially monodispersed assemblies having a mean diameter of less than about 100 nm, said assemblies comprising an albumin derivative comprising albumin having a hydrophobic polymer chain coupled thereto, said assemblies being crosslinked through the albumin, wherein the assemblies comprise a core comprising the polymer chains and a shell comprising the albumin and have an anti-cancer drug located at least partially in the core of the amphiphile assemblies.

In a second aspect of the invention there is provided a process for making a dispersion according to the first aspect, said process comprising providing the albumin derivative in an aqueous solution (optionally by combining the albumin derivative and the aqueous solution, or by preparing the albumin derivative in the aqueous solution) and allowing the albumin derivative to self-assemble so as to form the assemblies.

The following aspects may be used in conjunction with the second aspect, either individually or in any suitable combination.

The process may comprise the step of coupling the albumin to a polymeric reagent so as to prepare the albumin derivative. The polymeric reagent may comprise the polymer chain terminated with a coupling group or may comprise the polymer chain having a coupling group located away from a terminus thereof. The coupling may comprise for example one of the following reactions: cycloaddition of an alkyne to an azide to form a triazole; reaction of an alcohol with a carboxylic acid or a carboxylic acid halide to form an ester; reaction of an amine with a carboxylic acid or a carboxylic acid halide to form an amide; addition of a thiol to an alkene to form a thioether; reaction of an organometallic substance with an organic halide to form a C—C bond.

The process may comprise coupling an initiator group or chain transfer group to the albumin and either polymerising a monomer using the initiator group to initiate polymerisation, or polymerising a monomer in the presence of the albumin having the chain transfer group coupled thereto, so as to form the albumin derivative. The polymerisation may be conducted in the absence of or in the presence of a biological substance which is to be incorporated into the amphiphile assemblies.

The process may comprise polymerising a monomer in the presence of the albumin as a terminating agent so as to form the albumin derivative. In this event, the polymerisation may be an anionic polymerization or a ring-opening polymerization or some other type of polymerisation which may be terminated by the albumin.

The process may comprise combining the albumin derivative with a substance, e.g. a biologically active substance, so as to incorporate said substance into the assemblies. The step of combining the albumin derivative with the substance may be conducted before the step of allowing the albumin derivative to self-assemble. It may be conducted before combining the albumin derivative and the aqueous solution or it may be conducted simultaneously with said combining or may be conducted after said combining but before allowing the albumin derivative to self-assemble. In embodiments in which the process comprises the step of coupling the albumin to a polymeric reagent so as to prepare the albumin derivative, the process may additionally comprise combining the polymeric reagent with a biologically active substance prior to said coupling step so as to incorporate said biologically active substance into the amphiphile assemblies.

The step of combining the albumin derivative and the aqueous solution may comprise agitating the albumin derivative in the aqueous solution. The aqueous solution may comprise an organic solvent (preferably a water miscible organic solvent) in combination with water, or may contain no organic solvent, or may contain no solvent other than water.

The process may additionally comprise crosslinking the assemblies, commonly crosslinking the albumin. This may comprise exposing the assemblies to a dialdehyde.

In an embodiment there is provided a process for making a dispersion according to the first aspect, said process comprising coupling an albumin to a polymeric reagent so as to prepare an albumin derivative, combining the albumin derivative, a biologically active substance and an aqueous solution and allowing the albumin derivative to self-assemble so as to form the assemblies whereby the biologically active substance is located at least partially in the cores of the assemblies. This embodiment may comprise crosslinking the albumin with a dialdehyde after the formation of the dispersion.

In another embodiment there is provided a process for making a dispersion according to the first aspect, said process comprising combining a polymeric reagent and a biologically active substance, combining the resulting mixture with an albumin so as to couple the albumin with the polymeric reagent and thereby prepare an albumin derivative having the substance associated therewith, and allowing the albumin derivative to self-assemble so as to form the assemblies whereby the biologically active substance is located at least partially in the cores of the assemblies. This embodiment may comprise crosslinking the albumin with a dialdehyde after the formation of the dispersion.

In a third aspect of the invention there is provided a method of treating a condition in a subject, said method comprising administering to said subject an effective quantity of a dispersion of assemblies:
 according to the first aspect, said assemblies additionally comprising a biologically active substance, or
 made by the process of the second aspect, said process additionally comprising combining the albumin derivative with a biologically active substance so as to incorporate said substance into the assemblies,
wherein the biological substance is indicated for said condition.

In a fourth aspect of the invention there is provided use of a dispersion of assemblies for preparation of a medicament for the treatment of a condition in a subject, said dispersion being:
 according to the first aspect, said assemblies additionally comprising a biologically active substance, or
 made by the process of the second aspect, said process additionally comprising combining the albumin derivative with a biologically active substance so as to incorporate said substance into the assemblies,
wherein the biological substance is indicated for said condition.

In a fifth aspect of the invention there is provided a preparation for treatment of a condition in a subject, said preparation comprising a dispersion of assemblies according to the first aspect, said assemblies additionally comprising a biologically active substance, or
 made by the process of the second aspect, said process additionally comprising combining the albumin derivative with a biologically active substance so as to incorporate said substance into the assemblies,
wherein the biological substance is indicated for said condition.

In any or all of the third to fifth aspects, the condition may be an inflammation or a tumor. The subject may be a human subject or may be a non-human mammalian subject or may be a non-mammalian subject.

In a sixth aspect of the invention there is provided a method of delivering a substance to a liquid medium, said method comprising:
 preparing a dispersion of assemblies, said assemblies comprising an albumin derivative comprising albumin having a polymer chain coupled thereto, wherein the assemblies comprise a core comprising the polymer chains and a shell comprising the albumin, said dispersion having said substance disposed in the core of the assemblies of said dispersion, adding the dispersion to the liquid medium, and
allowing the substance to diffuse out of the assemblies of the dispersion.

The method may be a non-therapeutic method. It may be a non-diagnostic method. The liquid medium may be a medium that is not a biological medium.

In a seventh aspect of the invention there is provided a substance comprising a plurality of assemblies, said assemblies comprising an albumin derivative comprising albumin having a polymer chain coupled thereto, wherein the assemblies comprise a core comprising the polymer chains and a shell comprising the albumin.

The assemblies may be as described in the first aspect.

The substance may be in the form of a powder. It may have a water content of less than about 2% on a weight basis.

In an eighth aspect of the invention there is provided a pharmaceutical composition comprising the substance of the seventh aspect together with one or more pharmaceutically acceptable carriers, diluents and/or adjuvants.

The pharmaceutical composition may comprise a biological substance. The biologically active substance may be located at least partially in the core of the assemblies.

The pharmaceutical composition may be in the form of a powder. It may have a water content of less than about 2% on a weight basis.

In a ninth aspect of the invention there is provided a process for making a substance or a pharmaceutical composition according to the seventh or eighth aspect respectively comprising: providing a dispersion according to the first aspect; and drying said dispersion.

The step of drying may comprise freeze-drying. The drying may be conducted to a water content of less than about 2% by weight.

The step of providing the dispersion may comprise making the dispersion, for example by the process of the second aspect.

The substance or the pharmaceutical composition according to the seventh or eighth aspect respectively may be made by the process of the ninth aspect.

In a tenth aspect of the invention there is provided a process for making a dispersion according to the first aspect comprising: providing a substance according to the seventh aspect or a pharmaceutical composition according to the eighth aspect; and combining said substance or pharmaceutical composition with water or an aqueous solution.

The process may additionally comprise agitating the substance or pharmaceutical composition in the aqueous solution so as to disperse the substance in the aqueous solution.

DESCRIPTION OF EMBODIMENTS

Figure 1:
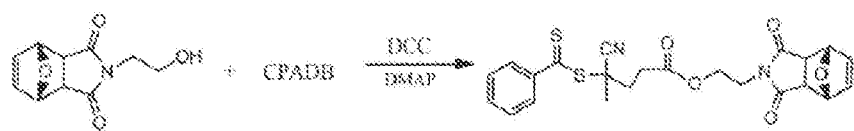
FIG. 1 shows a scheme of synthesis of protected maleimide end-functionalised CPADB RAFT agent from maleimide alcohol.

Albumin is increasingly used as a protein carrier for drugs. It facilitates targeting of drugs and improves the pharmacokinetic profile of drugs. Albumin is the most abundant plasma protein (35-50 g/L human serum) with a molecular weight of 66.5 kDa. The circulation time of human serum albumin (HSA) is very high with an average half-life of 19 days. HSA has many functions:
a) solubilises fatty acids
b) binds bilirubin, the yellow breakdown product of normal heme catabolism
c) binds many drugs
d) acts as transport vehicle for metal ions such as copper (II) and nickel(II)
e) regulates the colloid osmotic pressure of the blood
f) provides nutrition for tissue once it has been cleaved into amino acids Albumin is a slightly acidic and very soluble protein. The isoelectric point (IEP) is at pH=4.8, which means that albumin is negatively charged in blood. The protein is very robust: it is stable in the pH range of 4 to 9, soluble in 40% ethanol, and can be heated at 60° C. for up to 10 hours. The interest in albumin as drug carrier stems from its availability, its biodegradability, and its lack of toxicity and immunogenicity. A very intriguing aspect of albumins is their preferential uptake in tumor and inflamed tissue.

The product of the present invention may be made by attaching a polymer (optionally copolymer) chain onto an albumin molecule, so as to produce a molecule capable of self-assembly into particles which may be less than 200 nm, commonly less than 100 nm. The attaching may comprise bonding, e.g. covalently bonding, the polymer to the albumin molecule. The size of the particles may be adjusted by adjusting the size (e.g. molecular weight) of the polymer. Thus for a particular polymer chemistry, a lower molecular weight may be used in order to achieve smaller diameter particles. The process of the invention may therefore comprise the step of selecting a molecular weight of the polymer chain in order to obtain a desired particle size. The uptake into tumors of assembly having an albumin shell is superior to traditional micelles leading to higher toxicity to the tumors relative to other micelles. In a particular embodiment of the invention a hydrophobic chain is conjugated to albumin, so as to produce a structure that is amphiphilic (hydrophilic albumin, oil-soluble polymer chain) As a result, the structure is capable of self-assembly into assemblies, which are in general below 200 nm, commonly below 100 nm, in size. The inventors have encapsulated drugs into these assemblies, which have a core comprising polymer and a shell comprising albumin. The structure of the polymer in the core may be adjusted to the particular drug delivery challenge. The inventors have successfully demonstrated this technique for hydrophobic drugs and metal based drugs, however similar technology may also be used to deliver DNA or other hydrophilic substances, by adjusting the type of polymer. The core may be adjusted to any drug or other substance that needs to be delivered, e.g. an anti-cancer drug such as doxicyclin, paclitaxel, cisplatin or DNA, a peptide drug, or a proteinaceous drug. In this context it should be noted that in the present specification the term "comprise" and related words should be taken to indicate the presence of the designated integer and optionally other unspecified integers. The term encompasses the possibility that no such unspecified integers are present and therefore encompasses the term "consists of" or "consists essentially of".

In summary, albumin assemblies may be readily made having a smaller size than nab-albumin. The actual size of the assemblies may be adjusted by adjusting the length of the polymer chain. The core may be designed to suit a wide range of hydrophobic drugs, but, in contrast to nab-albumin, can also be tailored so as to encapsulate other drugs such as DNA. In the context of the present invention, an "assembly" is a self-assembled structure of molecules. These molecules are commonly amphiphiles, i.e. have a hydrophilic region (derived from albumin) coupled to a hydrophobic region (which is a polymer chain) so as to enable them to self-assemble. Examples of assemblies that may be made, or used, in accordance with the invention include micelles, rod-like micelles, vesicles, bilayer cylinders, bilayer sheets etc. In the case where the assemblies are not micelles, the "core" should be taken to be the region of the assembly occupied by the polymer chains. Similarly, in such cases, the "shell" should be taken to be the region of the assembly occupied by the albumin. In other words, the assemblies are such that the polymer chains of the albumin derivative are collected in a region designated the "core" and the albumin portions of the albumin derivative are collected in a region designated the "shell", which, in many, but not all, embodiments, surrounds, or substantially completely surrounds, or at least partially surrounds, the core. In some embodiments the polymer is hydrophilic. In such cases the assembly formation may be driven by the interaction of the polymer with the drug (e.g. by dipole-dipole interactions or by ionic attractions).

The present invention complements the nab-albumin technology that is presently available. A disadvantage of nab-albumin technology is that it is only suitable for encapsulation of hydrophobic drugs such as paclitaxel or doxorubicin. In addition, the particles are usually above 100 nm. The present technology therefore has the advantage that: 1) albumin assemblies may be constructed having a smaller size than nab-albumin, 2) the size of the assemblies may be adjusted by adjusting the length and nature of the polymer chain and 3) the core may be designed to suit all types of hydrophobic drugs (and in some cases hydrophilic drugs) so that, in contrast to nab-albumin, the assemblies of the present invention are also capable of encapsulating other drugs such as DNA, peptides etc. The present technology is capable of producing particles of less than 100 nm with albumin coating by adjusting the length of the polymer, and can also deliver other drugs such as siRNA, metal based drugs or peptides. Smaller particles such as those afforded by the present invention are more suitable for treatment of cancers that respond better to small particle such as pancreatic cancer.

The present invention discloses a dispersion of assemblies. In this context, the term "dispersion" indicates that the assemblies are dispersed in the dispersion. The dispersion may comprise a continuous phase and the assemblies may represent a discontinuous phase dispersed through the continuous phase. The continuous phase may be a liquid or may be a gel or may be some other type of continuos phase. The dispersion may therefore be an emulsion, or may be a microemulsion, or may be a suspension. The assemblies may be substantially homogeneously dispersed through the continuous phase of the dispersion. The dispersion may be a liquid or may be a gel or may be in some other physical form. The proportion of assemblies in the dispersion may be between about 0.1 and about 50% on a volume/volume basis, or between about 0.1 and 10, 0.1 and 5, 0.1 and 1, 1 and 50, 5 and 50, 10 and 50, 1 and 20, 1 and 10, 1 and 5, 5 and 20 or 10 and 20%, e.g. about 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45 or 50% or may in some instances be over 50%. The continuous phase may be aqueous. It may contain no organic solvents. It may comprise salts. It may comprise buffers. It may have a pH of about 2 to about 12, or about 2 to 7, 7 to 12, 3 to 11, 4, to 10, 5 to 9, 6 to 8, 4 to 7, 7 to 10 or 7 to 8, e.g. about 2, 2.5, 3, 3.5, 4, 4.5, 5, 5.5, 6, 6.5, 7, 7.5, 8, 8.5, 9, 9.5, 10, 10.5, 11, 11.5 or 12.

The inventors have discovered that the dispersion of the present invention may be dried. This facilitates storage. Commonly the process of drying the dispersion will comprise freeze-drying. The dried dispersion may be in the form of a powder, commonly a free-flowing powder. It may have a water content of less than about 5% on a weight basis, or less than about 4, 3, 2 or 1%, or about 1 to 5 or 1 to 3%, e.g. about 5, 4, 3, 2, 1, 0.5 or 0.1%. The dried dispersion may be readily redispersed in water or suitable aqueous solution, so as to produce an aqueous dispersion of the assemblies. The redispersing may simply involve addition of the water or suitable aqueous solution. It may additionally comprise agitating the resulting mixture so as to disperse the assemblies. The agitation may comprise one or more of swirling, shaking, stirring or sonicating. The agitation may be conducted for sufficient time and with sufficient vigour or power to completely disperse the assemblies in the water or aqueous solution. The dried dispersion may additionally comprise suitable additives. These may be suitable for pharmaceutical use, for example adjuvants. They may include dessicants or other suitable additives. It should be noted that where reference is made in this specification to "dissolving" the assemblies or albumin, this may include formation of a micellar solution, i.e. may include micellisation.

These assemblies comprise, optionally consist essentially of, an albumin derivative (and optionally also water), and also optionally have a biologically active substance associated with said derivative. The derivative comprises, optionally consists essentially of, albumin having a polymer chain coupled thereto. The assemblies comprise a core comprising the polymer chains and a shell comprising the albumin. The core may consist essentially of the polymer chains, together with the biologically active substance (if present). The shell may consist essentially of the albumin, optionally also together with bound water and/or bound ions.

The assemblies of the present invention comprise molecules having an albumin molecule coupled to, optionally bonded (e.g. covalently bonded) to, a polymer chain. The albumin molecule may be any suitable album. It may be a serum albumin, for example bovine serum albumin or human serum albumin. It may be a storage albumin, e.g. ovalbumin. The polymer chain may be attached through a terminal monomer group in the chain or may be attached through a non-terminal monomer group in the chain. Suitable coupling chemistries will be dictated by the nature of the polymer chain and the available functional groups on the albumin. A particularly suitable group on the albumin molecule for coupling is the thiol group, in particular the thiol group on a cysteine group (e.g. cysteine-34) in the albumin molecule. The skilled person will readily appreciate which groups on a polymer chain may be suitable for coupling to particular groups in the albumin molecule, in particular to a thiol group.

The polymer chain may be any type of polymer chain capable of coupling to the albumin. It may be hydrophilic or it may be hydrophobic. In the case where the polymer chain is hydrophilic, it may be charged (either positively or negatively) or may be zwitterionic. It may be functionalised so as to associate with (e.g. complex with) a desired biologically active substance. Commonly it is not a polyethyleneglycol chain. More generally it may be a chain that is not a hydrophilic polyglycol chain, or that is not a non-ionic hydrophilic chain.

Suitable hydrophobic chains include acrylate and methacrylate chains (e.g. methyl, ethyl, propyl, butyl or phenyl acrylate or methacrylate), polyolefin chains (e.g. ethylene, propylene, butylene, butadiene or hexene), polyether chains (e.g. methylvinyl ether, phenylvinyl ether), polyester chains (e.g. polylactide), polyamide chains (e.g. nylon-6, nylon-6, 6, nylon-4,6, nylon-11), polystyrene chains (optionally substituted) or some other suitable polymer chain. Copolymers, either random or block, are also envisaged. In some instances the polymer, or one of the polymeric units in a copolymer, may contain functional groups capable of binding or complexing a substance to be encapsulated in the assemblies. For example diamine groups may be used to complex metals such as platinum which are to be incorporated into the assemblies.

Suitable hydrophilic chains include polypeptides and polyelectrolytes, e.g. polyamines (optionally polyquaternary ammonium), polycarboxylic acids etc.

The molecular weight of the polymer chain may be adjusted so as to obtain a desired size of amphiphile assembly. Thus a longer polymer chain of the same chemical nature will in general result in larger amphiphile assemblies. Commonly the molecular weight will be from about 1000 to about 1,000,0000, or about 1000 to 1000000, 1000 to 500000, 1000 to 100000, 1000 to 50000, 1000 to 20000, 1000 to 10006, 1000 to 5000, 1000 to 2000, 2000 to 1000000, 5000 to 1000000, 10000 to 1000000, 50000 to 1000000, 100000 to 1000000, 5000 to 100000, 5000 to 50000, 5000 to 10000, 10000 to 50000, 10000 to 100000 or 20000 to 50000, e.g. about 1000, 2000, 3000, 4000, 5000, 6000, 7000, 8000, 9000, 10000, 15000, 20000, 25000, 30000, 35000, 40000, 50000, 60000, 70000, 80000, 90000, 100000, 200000, 500000 or 1000000. In some cases the molecular weight may be greater than or less than the above ranges. This may be a number average or a weight average molecular weight. The polymer chain may have an average degree of polymerisation of about 10 to about 100, or about 10 to 50, 10 to 20, 20 to 50, 20 to 100 or 50 to 100, e.g. about 10, 20, 30, 40, 50, 60, 70, 80, 90 or 100, or may be more than or less than those ranges. The polymer chain may be essentially monodispersed, or may have a distribution of molecular weights. It may have a polydispersity (defined as the ratio between weight average and number average molecular weights) of less than about 1.1, or less than about 1.2, 1.3, 1.4, 1.5, 1.6, 1.7, 1.8, 1.9 or 2, or of about 1 to about 2, or about 1 to 1.5, 1 to 1.2, 1.2 to 2, 1.5 to 2 or 1.2 to 1.5, e.g. about 1, 1.1, 1.2, 13, 1.4, 1.5, 1.6, 1.7, 1.8, 1.9 or 2, or may be greater than about 2. The synthesis of the polymer chain may be by means of a living polymerisation technique such as RAFT (Reversible Addition-Fragmentation chain-Transfer) polymerisation. It may be by means of a polymerisation technique which introduces a functional endgroup, e.g. an endgroup capable of coupling to albumin or capable of being converted to a group capable of coupling to albumin, or may be by means of a polymerisation technique which introduces a non-terminal functional group capable of coupling to albumin or capable of being converted to a group capable of coupling to albumin.

The coupling between the albumin and the polymer chain may be any suitable coupling, e.g. an ester, an ether, an amide, a thioether, a triazole, a siloxane or other suitable coupling.

The assemblies of the present invention may have a mean diameter of less than about 200 nm, or less than about 150, 100, 90, 80, 70, 60 or 50 nm, or of about 25 to about 200 nm, or about 25 to 50, 25 to 75, 25 to 100, 50 to 200, 50 to 150, 50 to 100, 50 to 75, 75 to 200, 100 to 200, 100 to 150 or 75 to 150 nm, e.g. about 25, 30, 40, 50, 60, 70, 80, 90, 100, 110, 120, 130, 140, 150, 160, 170, 180, 190 or 200 nm. In some instances, the amphiphile assemblies may have a mean diameter of greater than 200 nm, e.g. about 250, 300, 350, 400, 450 or 500 nm. As discussed elsewhere, by suitable choice of the chemical nature of the polymer chain and its degree of polymerisation, the mean diameter may be varied at will to suit a specific application. The assemblies may be essentially monodispersed in diameter, or may have a distribution of diameters. They may have a polydispersity (defined as the ratio between weight average and number average diameters) of less than about 1.1, or less than about 1.2, 1.3, 1.4, 1.5, 1.6, 1.7, 1.8, 1.9 or 2, or of about 1 to about 2, or about 1 to 1.5, 1 to 1.2, 1.2 to 2, 1.5 to 2 or 1.2 to 1.5, e.g. about 1, 1.1, 1.2, 1.3, 1.4, 1.5, 1.6, 1.7, 1.8, 1.9 or 2, or may be greater than about 2. The assemblies may be spherical, or may be substantially spherical, or may be oblate spherical, polyhedral, acicular, disc-shaped, torroidal, or some other shape. In the event that the assemblies are not spherical, the above mean diameters may be hydrodynamic diameters, or may be the mean of the maximum or minimum diameters of the assemblies. It should be noted that, as stated elsewhere herein, for treatment of tumours, particle diameters of the assemblies of less than about 100 nm may be preferred. However there is still value in some instances in preparing assemblies of greater than 100 nm, particularly when these are tailored to incorporate bioactive substances which have hitherto been difficult to incorporate into albumin-based assemblies, e.g. hydrophilic molecules such as DNA, RNA etc.

The assemblies may comprise a drug or other bioactive (i.e. biologically active) substance. Suitable drugs include those which are active in treatment of inflammations or of tumors. Particularly suitable drugs include anticancer drugs. Mixtures of drugs may also be used. The ratio of polymer (i.e. polymer chain) to drug may be about 5 to about 50 (i.e. 5:1 to about 50:1) on a weight basis, or about 5 to 20, 5 to 10, 10 to 20, 10 to 50, 20 to 50 or 20 to 30, e.g. about 5, 10, 15, 20, 25, 30, 35, 40, 45 or 50. Commonly the bioactive substance will be located at least partially, optionally primarily (e.g. greater than about 50%, or greater than about 60, 70, 80, 90 or 95%) in the core of the assemblies. It may be associated with the polymer chains in the core of the assemblies. In the case of a hydrophobic polymer core, the bioactive substance may be hydrophobic and hence may partition preferentially to the core of the assemblies. In other cases the polymer chains are ionically charged. In this case the bioactive substance may have a charge opposite to that on the polymer chains so that it partitions preferentially to the core of the assemblies due to ionic attraction. Thus the bioactive substance may represent a counterion to charged polymer chains in the core of the assemblies. The bioactive substance may be positively charged and the polymeric chains negatively charged (e.g. carboxylate or sulfonate functional) or the bioactive substance may be negatively charged and the polymeric chains positively charged (e.g. quaternary ammonium functional). In some instances the bioactive substance may be complexed (or complexable) to the polymer chains. This may be particularly suitable in cases where the bioactive substance is a metal. The skilled person will readily recognise suitable complexing groups which may be present, or may be introduced, in the polymer chains. Frequently these will include diamine or polyamines suitable for bidentate or polydentate complexation.

The assemblies of the present invention may be made by combining an albumin derivative and an aqueous solution and allowing the albumin derivative to self-assemble to form the assemblies. As discussed, the albumin derivative comprises albumin having a polymer chain attached thereto. In a particular embodiment, the polymer chain is attached through a terminal monomer unit thereof to a thiol group on the albumin molecule. The self-assembly step may simply involve allowing the derivative to stand in the aqueous solution or it may comprise agitating the derivative in the aqueous solution, e.g. stirring, swirling, shaking, sonicating or other form of agitating, or combinations of forms of agitation may be used. It may require some time for formation of the assemblies, e.g. at least about 6 hours, or at least about 12, 24, 36 or 48 hours, or about 6 to about 60 hours, or about 6 to 48, 6 to 24, 12 to 60, 24 to 60, 48 to 60 or 24 to 48 hours, e.g. about 6, 12, 18, 24, 36, 42, 48, 54 or 60 hours. It will be understood that the time will depend on the temperature, and higher temperatures may require less time for the self-assembly step.

The process may comprise the step of preparing the albumin derivative. This may be accomplished by coupling a polymer (i.e. polymeric reagent) to albumin. As noted above, the albumin may be any suitable albumin, commonly a serum albumin such as BSA (bovine serum albumin) or HSA. In some cases it may be necessary to functionalise the albumin or the polymer or both in order to provide suitable groups for coupling. A convenient group on albumin for coupling is the thiol group. This may be coupled to suitable polymers by a thiol-ene reaction, thioesterification, oxidative coupling of thiols or thioether formation. For such reactions, the polymer should be functionalised with a suitable functional group, e.g. an olefin such as maleimide, a carboxylic acid or equivalent, a thiol or a halide.

Other coupling reactions suitable for coupling the polymer to the albumin are well known. These include cycloaddition of an alkyne to an azide to form a triazole; reaction of an alcohol with a carboxylic acid or a carboxylic acid halide to form an ester; reaction of an amine with a carboxylic acid or a carboxylic acid halide to form an amide; addition of a thiol to an alkene to form a thioether; reaction of an organometallic substance with an organic halide to form a C—C bond. It will be understood that for some of these it is necessary to functionalise the albumin appropriately. This may commonly be achieved by reacting a thiol on the albumin molecule with a suitable compound so as to introduce the desired functional group into the albumin.

In some cases, the polymer prior to coupling to the albumin will be insoluble in water. It may be necessary to dissolve it in a solvent, commonly an organic solvent, prior to mixing it with an aqueous solution of the albumin. The organic solvent is preferably miscible or at least partially miscible with water. Suitable such solvents include DMSO, DMF, HMPT, HMPA, acetone and THF. Commonly as little as possible of the organic solvent will be used. The solution of albumin, which is aqueous, may contain salts, commonly buffers such as PBS.

The coupling may be conducted at any suitable temperature. It may be conducted at room temperature, or between about 10 and about 50° C., or about 10 to 30, 10 to 20, 20 to 50, 30 to 50 or 20 to 30° C., e.g. at about 10, 15, 20, 25, 30, 35, 40, 45 or 50° C. The temperature used should, however, not be sufficient to denature the albumin. It may be sufficiently low as to not denature a bioactive substance in the assemblies. The time for the coupling may be with the same range as for self-assembly to form the assemblies as described earlier. Commonly the steps of coupling and self-assembly will be conducted in a 'one-pot' process rather than in two discrete steps.

Another approach to preparing the albumin derivative comprises coupling an initiator group to the albumin and then using the resulting albumin bound initiator to initiate polymerisation of a monomer to form a polymer chain attached to the albumin moiety. Suitable initiator groups that may be attached to albumin for this purpose include thiocarbonyl thio groups (for RAFT polymerisations), aminoxy groups (for nitroxide mediated polymerisations), an active halide (e.g. alpha-halo carbonyl or benzyl halide, for ATRP polymerisation) etc.

A further approach to preparing the albumin derivative comprises coupling a chain transfer group to the albumin and polymerising a monomer in the presence of the albumin bound chain transfer group. Suitable chain transfer groups which may be used in this case include thiols and halides. It should be noted that albumin contains thiols, and may therefore be used as a chain transfer agent without further elaboration.

Yet another approach to preparing the albumin derivative comprises polymerising a monomer in the presence of the albumin as a terminating agent so as to form the albumin derivative. In this event, the polymerisation may be an anionic polymerization or a ring-opening polymerization or some other type of polymerisation which may be terminated by the albumin.

In any of the above approaches to forming the assemblies, the process may comprise the step of selecting a suitable chemistry of the polymer chain so as to bind a desired biologically active substance or to encapsulate the biologically active substance in the resulting assemblies. It may comprise the step of selecting a suitable molecular weight, or degree of polymerisation, of the polymer chain so as to produce assemblies of desired diameter or size. It may comprise using suitable polymerisation conditions as to obtain the desired molecular weight, or degree of polymerisation, of the polymer chain.

In certain embodiments the assemblies contain a substance, e.g. a biologically active substance. The substance may be releasable from the assemblies. In order to load this substance into the assemblies, the assemblies may be formed in the presence of the substance or the substance may be added to the preformed assemblies so as to penetrate into the assemblies, commonly into the cores thereof. Thus in some embodiments, the process comprises combining the substance, optionally in solution, albumin and a polymer and agitating the resulting mixture for sufficient time and at suitable temperature for formation of assemblies comprising albumin-polymer conjugates together with the substance. In other embodiments the process comprises combining albumin and a polymer and agitating the resulting mixture for sufficient time and at suitable temperature for formation of assemblies comprising albumin-polymer conjugates, adding the substance, optionally in solution, and allowing the substance to penetrate into the assemblies so as to form assemblies comprising albumin-polymer conjugates together with the substance. In particular embodiments, the polymer may be combined with the substance, optionally coupled (e.g. complexed) thereto, prior to addition of or to the albumin. Thus the albumin may be coupled with a complex or conjugate comprising the polymer and the substance.

The process may comprise the step of producing the polymer prior to coupling the polymer to the albumin. In many cases this will involve a controlled polymerisation for example a controlled radical polymerisation. Suitable controlled radical polymerisation methods include RAFT (reversible addition-fragmentation chain transfer polymerisation), ATRP (atom transfer polymerisation), nitroxide-mediated polymerisation etc. These are well known to those skilled in the art. By adjusting the ratio of monomer to initiator, it is commonly possible to control the molecular weight of the polymer and at times the polydispersity thereof. This may in turn be used to control the diameter of the resulting assemblies as required.

The dispersion of the present invention may be used for delivering an encapsulated substance. An advantage of the present invention is that the albumin shell of the assemblies is preferentially taken up in tumors and sites of inflammation. Thus the assemblies are suited for delivering substances to such loci. Accordingly, suitable substances for incorporation into the assemblies include anti-cancer drugs, anti-inflammatory drugs and combinations of these. In this context, a drug may be considered as any substance capable of treating the particular condition (cancer, inflammation). It may be an organic substance, an inorganic substance, an ionic substance, a metallic substance, an organometallic substance or may be a combination or mixture of any two or more of these or may be more than one of these. The substance may be releasable from the assemblies. It may be releasable over an extended time, e.g. over a time of from about 1 minute to about 1 month. The extended time may be for example about 1, 2, 3, 4, 5, 10, 20, 30, 40 or 50 minutes, or about 1, 2, 3, 4, 5, 6, 12, or 18 hours or about 1, 2, 3, 4, 5 or 6 days or 1, 2, 3 or 4 weeks, or may be some other time. It may be a time on the order of minutes, hours, days, weeks or months.

Following formation of the assemblies, they may be crosslinked. This may serve to render them more resilient, or less likely to disintegrate, or more resistant to aggressive environmental conditions (e.g. temperature, pressure, pH, protein denaturing agents etc.). The step of crosslinking may comprise crosslinking the albumin portions of the albumin derivatives molecules. It may comprise exposing the assemblies to a crosslinking agent under suitable crosslinking conditions. The crosslinking agent may be a compound having at least two (optionally 3, 4 or 5 or more than 5) functional groups capable of reacting with functional groups on the albumin, e.g. capable of reacting with amine groups on the albumin. Examples of such crosslinking agents include dialdehydes. These may be of formula CHO—$(CH_2)_n$—CHO. In this formula, n may be an integer from 0 to 10, e.g. 0, 1, 2, 3, 4, 5, 6, 7, 8, 9 or 10. A suitable crosslinking agent is glutaraldehyde. In this instance, the crosslinking may simply require exposure of the assemblies to aqueous dialdehyde at ambient temperature, or for example about 20 to about 50° C.

The crosslinking may be conducted before loading the assemblies with a bioactive substance or may be conducted after loading the assemblies with a bioactive substance or may be conducted concurrently with the step of loading the assemblies with a bioactive substance. The step of crosslinking may be conducted at ambient temperature or at any other suitable temperature.

At any suitable stage during or after the formation of the assemblies, unreacted starting materials such as uncoupled polymer, uncoupled albumin, excess crosslinker (if used) or unbound substance, may be removed by a suitable means. The suitable means will depend on the stage of formation and the nature of the material to be removed, and may include one or more of filtration, centrifugation, microfiltration, ultrafiltration, settling and dialysis.

The dispersion of assemblies described herein may be used for manufacturing a medicament for treatment of cancer or for treatment of inflammation or both. It will be understood that to do so, the assemblies should contain a suitable substance for treating the cancer or inflammation or both. The invention also encompasses the use of the dispersion for the treatment of a condition in a patient, commonly for the treatment of a cancer or inflammation. The cancer may be a primary cancer or may be a metastatic cancer. It may be bladder cancer, breast cancer, colorectal cancer, endometrial cancer, kidney cancer, liver cancer, leukemia, lung cancer, melanoma, other skin cancer, non-Hodgkin lymphoma, pancreatic cancer, prostate cancer or thyroid cancer, or may be some other cancer. The patient may be a human or may be a non-human. The patient may be a non-human primate or non-human mammal or non-mammal.

The invention also encompasses a pharmaceutical or veterinary composition for treatment of a condition, e.g. cancer or an inflammation, comprising the dispersion of the present invention. The composition may additionally comprise one or more additives, e.g. one or more pharmaceutically or veterinarily acceptable carriers, diluents and/or adjuvants.

In use of such a composition for treatment of a condition, it will be apparent to one of ordinary skill in the art that the optimal quantity and spacing of individual dosages will be determined by the nature and extent of the disease state being treated, the form, route and site of administration, and the nature of the particular individual being treated. Also, such optimum conditions can be determined by conventional techniques.

It will also be apparent to one of ordinary skill in the art that the optimal course of treatment, such as, the number of doses of the composition given per day for a defined number of days, can be ascertained by those skilled in the art using conventional course of treatment determination tests.

These compositions can be administered by standard routes. In general, the compositions may be administered by the parenteral (e.g., intravenous, intraspinal, subcutaneous or intramuscular), oral or topical route. In some cases the administration may be by direct injection to the diseased site, e.g. direct injection into a tumor.

The carriers, diluents and adjuvants should be "acceptable" in terms of being compatible with the other ingredients of the composition, and not deleterious to the recipient thereof.

Examples of pharmaceutically acceptable carriers or diluents are demineralised or distilled water; saline solution; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; polyvinylpyrridone; agar; carrageenan; gum tragacanth or gum acacia, and petroleum jelly. Typically, the carrier or carriers will form from 10% to 99.9% by weight of the compositions.

The compositions of the invention may be in a form suitable for administration by injection, in the form of a formulation suitable for oral ingestion (such as capsules, tablets, caplets, elixirs, for example), in an aerosol form suitable for administration by inhalation, such as by intranasal inhalation or oral inhalation, in a form suitable for parenteral administration, that is, subcutaneous, intramuscular or intravenous injection, or in the form of a suppository.

For administration as an injectable solution or suspension, non-toxic parenterally acceptable diluents or carriers can include, Ringer's solution, isotonic saline, phosphate buffered saline, ethanol and 1,2 propylene glycol.

Adjuvants typically include emollients, emulsifiers, thickening agents, preservatives, bactericides and buffering agents.

Methods for preparing parenterally administrable compositions are apparent to those skilled in the art, and are described in more detail in, for example, Remington's Pharmaceutical Science, 15th ed., Mack Publishing Company, Easton, Pa., hereby incorporated by reference herein.

Example 1

Polymer-protein amphiphiles were prepared having maleimide-terminated poly(methyl methacrylate) (PMMA) chains extended via Reversible Addition-Fragmentation Chain-Transfer (RAFT) polymerisation and then conjugated to Bovine Serum Albumin (BSA) via thiol-ene reaction with the deprotected maleimide functionality of the polymer. Conversion of monomer was determined by 1H-NMR Spectroscopy and Gel Permeation Chromatography (GPC). Deprotection of the maleimide moiety to increase polymer functionality was confirmed by 1H-NMR Spectroscopy.

Model biofunctional micelles were developed from the self-assembly of the amphiphiles with hydrophobic PMMA cores and hydrophilic BSA shells for the encapsulation of hydrophobic Curcumin anti-cancer drugs. Blank aggregates produced particle diameters as low as 44 nm as measured by Dynamic Light Scattering (DLS). Preliminary Curcumin-encapsulated aggregates with a drug to polymer ratio of 1:15 produced particles of 51 nm and 69 nm for PMMA-3000 and 5000 chains respectively. TEM analysis was undertaken to confirm the structures of the aggregates in solution. The encapsulation efficiency and drug release of Curcumin was monitored using UV-Vis Spectroscopy. Cytotoxicity studies revealed that the Curcumin-loaded aggregates had a more pronounced effect on cancer cells as compared to free Curcumin, requiring just 59% and 32% (for PMMA-3000 and PMMA-5000 aggregates) of the amount of free Curcumin required to inhibit cell growth by 50%.

Harmful side-effects, low drug efficacy, and drug-resistance in cancer cells are often the result of traditional anti-carcinogenic drugs, and so recent research has been directed into improving their cellular uptake in cancerous cells. The anti-carcinogenic properties of the polyphenol Curcumin derived from Turmeric are well known, however its severe hydrophobicity results in poor solubility, rapid removal by the immune system and poor circulation times within the bloodstream. To overcome these limitations a range of nano-sized targeted drug-delivery mechanisms may be used to carry the drugs through the body virtually undetected. The drugs are ideally released from the carriers after preferentially accumulating in tumorous areas by the Enhanced Permeability and Retention Effect to cause the death of cancerous cells with minimal exposure to healthy bodily cells.

Amphiphilic block copolymers are promising and widely studied molecules for such carriers, which under the right environmental conditions and block configurations can self-assemble to form polymeric micelles with hydrophilic outer shells that facilitate passage through the bloodstream, and cores which can solubilise hydrophobic drugs. Due to their unique size range (as low as 20-150 nm), polymeric micelles are able to overcome multiple biological barriers, such as avoidance of the Mononuclear Phagocyte System (typically less than 100 nm).

It was considered a promising avenue to build on these structures by replacing these hydrophilic surfaces with aqueous human proteins such as albumin, which might significantly increase biofunctionality and circulation time in the body, and thus the effectiveness of the anticancer drugs. The inherent specificity of proteins in biological systems makes them suitable for use as therapeutic agents and potentially overcomes these issues experienced with traditional polymeric micelles, and the attachment of polymer chains to proteins can significantly improve properties such as stability.

Of the vast range of polymerisation methods available, Reversible Addition-Fragmentation Chain-Transfer Polymerisation (RAFT) shows great promise in the development of these polymer-protein conjugate carrier systems. The high level of control in RAFT polymerisation allows the creation of a variety of desired sizes and shapes of polymers much more easily than conventional methods, and its 'living' nature allows easy conjugation to other structures such as proteins.

The present experiment illustrates a systematic approach to the development of a drug carrier system for the hydrophobic drug Curcumin. Polymer-protein conjugates are synthesised through the thiol-ene click reaction of a tailored deprotected maleimide functional end-group PMMA chain, extended via RAFT polymerisation, to Bovine Serum Albumin. The amphiphiles are self-assembled in aqueous solution to form aggregates of a desirable size. The encapsulation efficiency, release rate and in vitro cytotoxicity of Curcumin post-encapsulation are evaluated, and optimal carrier-system characteristics are investigated.

Experimental

Materials

Unless otherwise specified, all chemicals were reagent grade and used as received. 4',4-azobis(4-cyanopentanoic acid) (Fluka, 98%), 4-(dimethylamino)pyridine (Aldrich, >99%), acetonitrile (Aldrich, 99.8%), AIBN (azo-bisisobutyronitrile, Aldrich, 99.8%), anhydrous methanol (Sigma-Aldrich, 99.8%), benzyl chloride (Aldrich, 99%), bovine serum albumin (Sigma, >96%), chloroform-D (CIL, 99.8%), copper (II) sulphate pentahydrate (BDH, 99.5%), Curcumin (Sigma), diethyl ether (Ajax, 98%), dimethylacetamide (Sigma-Aldrich, 99.9%), dimethyl sulfoxide (Ajax, 98%), elemental sulphur (Ajax, 98%), ethanolamine (Ajax, 97%), ethyl acetate (Ajax, 99%), furan (Aldrich, >99%), hydrochloric acid (Ajax, 31.5% w/w), maleic anhydride (Fluka, >99%), n-Hexane (Ajax, >95%), N,N-dimethylformamide (Ajax, 99.8%), N,N'-dicyclohexylcarbodiimide (Aldrich, 99%), PEGMEMA (Aldrich), petroleum ether (Ajax, >95%), potassium ferricyanide (Sigma-Aldrich, 99%), pyroneg (Johnson Diversey), silica gel (Sigma-Aldrich, 60 Å, 70-230 mesh), sodium hydroxide (Fluka, 0.1 M), sodium methoxide (Fluka, >97%), sodium phosphate dibasic (Sigma-Aldrich, 98%), sodium phosphate monobasic (Sigma-Aldrich, >99%), tetrahydrofuran (Fisher Scientific, HPLC Grade, >99.9%), and toluene (Ajax, 99%) were used as received. Methyl methacrylate (Aldrich, 99%, <30 ppm MEHG inhibitor) was purified by passing through a column of activated basic alumina to remove inhibitor.

Analysis.

Proton Nuclear Magnetic Resonance (1H-NMR) Spectroscopy.

All NMR measurements were performed using a Bruker DPX-300 with a $^1$H/X inverse broadband z gradient BBI probe at 300 MHz frequencies and using 16 scans as default. Samples were dissolved and analysed in deuterated chloroform ($CDCl_3$).

Dynamic Light Scattering (DLS).

DLS was performed by preparation of 1 mg·mL$^{-1}$ aqueous solutions of protein-polymer aggregates filtered through 0.45 µm filters and analysis on a Brookhaven ZetaPlus® Particle Sizer at 25° C. with a Dust-Cutoff of 40.

Gel Permeation Chromatography (GPC).

GPC was performed using a Shimadzu modular system containing a DGU-12A degasser, an LC-10AT pump, an SIL-10AD automatic injector, a CTO-10A column oven and a RID-10A refractive index dector. A 50×7.8 mm guard column and four 300×7.8 mm linear columns (500, $10^3$, $10^4$, $10^5$ Å pore size, 5 µm particle size) were used for analyses. N,N-dimethylacetamide (HPLC grade, 0.05% w/v BHT, 0.03% w/v LiBr) with a flow rate of 1 mL·min$^{-1}$ was used as the mobile phase. The injection volume was 50 µL. The samples were prepared by dissolving 2-3 mg·mL$^{-1}$ of the analyte in N,N-dimethylacetamide, followed by filtration through a 0.45 µm filter. The unit was calibrated using commercially available linear polystyrene standards (0.5-1000 kDa, Polymer Laboratories).

Transmission Electron Microscopy (TEM).

TEM analyses were performed using a JEOL1400 TEM at 80-100 kV beam voltage. Samples were prepared by placing a droplet of solution on formamide and graphite-coated copper grids and draining the excess using filter paper. Stained samples were exposed to uranyl acetate (3% aqueous solution) for 20 seconds once completely dry.

Ultraviolet-Visible Spectroscopy (UV-Vis).

UV-Vis measurements were performed on a double-beam Varian Cary-300 UV-Vis Spectrophotometer (PerkinElmer Differential Scanning calorimeter) (<5 Abs, $\lambda$=190-900 nm) over the visible range ($\lambda$=400-800 nm) at 25° C. Samples containing Curcumin were dissolved in N,N-dimethylformamide and measured in a quartz cell with a 10 mm path length.

Synthesis and Methods.

Synthesis of Protected Maleimide CPADB RAFT agent. Maleic anhydride (30.0 g, 306 mmol) was suspended in 150 mL of toluene and the mixture warmed to 80° C. Furan (33.4 mL, 459 mmol) was added via syringe and the turbid solution stirred for 24 hours in an oil bath at this temperature. After cooling for 1 hour at ambient temperature the resulting white crystals were collected by filtration and washed with 2×30 mL of petroleum ether to obtain 44.4 g (267 mmol, 87% yield) of small white needles. To a dry 100 mL round-bottomed flask, this was added (10.0 g, 60.2 mmol) with anhydrous methanol (20 mL) and ethanolamine (3.68 g, 60.2 mmol). The mixture was brought to reflux under stirring and the solution turned dark orange. After 24 hours, the reaction mixture was cooled to room temperature and product began to crystallize after 2 hours. The mixture was stored in the freezer overnight, and the precipitate was collected by vacuum filtration. The filtrate volume was reduced by rotary evaporation and allowed to crystallize, and a second crop of crystals was collected (yield 59%). This protected maleimide alcohol (0.25 g, 1.2 mmol), CPADB (4-cyanopentanoic acid dithiobenzoate, 0.29 g, 1.1 mmol), and DMAP (4-dimethylaminopyridine, 14 mg) were dissolved in dry THF (20 mL). DCC (dicyclohexylcarbodiimide, 0.27 g) was then added and the reaction mixture was stirred at room temperature for 4 hours. The reaction was monitored by TLC (hexane:EtOAc=2:1) and the third spot was the product. The reaction mixture was filtered to remove the white precipitate. The filtrate was concentrated enough to afford crude red oil and the crude was further purified by silica column chromatography (using 3:1 hexane:EtOAc to wash out the first two side product and 1:1 hexane:EtOAc to wash out the target compound) (0.34 g). $^1$H NMR (300 MH$_z$, CDCl$_3$) S=7.75 (t, 2H), 7.42 (t, 1H), 7.25 (t, 2H) 6.38 (t, 2H), 5.12 (t, 2H), 4.13 (t, 2H), 3.60 (t, 2H), 2.70 (m, 2H), 2.2-2.5 (m, 4H), 1.78 (s, 3H)

Polymerisation of Methyl Methacrylate with Protected Maleimide RAFT Agent.

Protected maleimide RAFT agent (70 mg, 0.148 mmol), AIBN initiator (4.89 mg, 0.03 mg) and methyl methacrylate monomer (447 mg, 4.47 mmol) were dissolved in toluene and the polymerisation was carried out at 70° C. for 20 hours under an inert, dry atmosphere. After quenching the reaction with liquid nitrogen and letting in air, the mixture was dried in an aluminium pan in a vacuum oven overnight at 40° C. $^1$H-NMR Spectroscopy was used to determine conversion. $^1$H NMR (300 MHz, CDCl$_3$) $\delta$=6.30 (s, 1H), 5.72 (s, 1H), 3.78 (t, 3H), 1.30 (s, 1H)

Deprotection of End-Functionalised Poly(Methyl Methacrylate).

2 g of polymer was dissolved in 10 mL toluene and the solution was brought to reflux for 24 hours. The solvent was evaporated and further dried in a vacuum oven at 40° C. overnight to afford the target maleimide-terminated PMMA. The formation of the deprotected maleimide group was confirmed by $^1$H-NMR with the presence of a new proton peak at near 6.5.

Conjugation of Bovine Serum Albumin to Poly(Methyl Methacrylate) Polymer Chains.

Polymer (0.8 μmol) was dissolved in 2 mL of DMSO and the solution was added dropwise over 4-6 hours via syringe pump into a solution of bovine serum albumin (0.5 mol, 34 mg) in 8 mL of PBS buffer (0.1 M, pH 7.0) under stirring. The mixture was stirred for 48 hours and subsequently dialyzed against deionised water using a MWCO=14000 dialysis membrane. After dialysis, the mixture was subjected to a brief sonication for 5 min and centrifugation (2000 g×5 min) to remove un-reacted PMMA polymer, and passed through a 0.45 μm (Millipore) filter to remove large particles.

Measurement of Encapsulation Efficiency and Drug Release Rate.

The conjugation of Bovine Serum Albumin to deprotected Poly(Methyl Methacrylate) chains was repeated, this time with the incorporation of Curcumin (0.16 μmol) dissolved in DMSO into the PMMA/DMSO solution before reaction. A calibration curve was created testing the absorbance of a range of concentrations of Curcumin dissolved in DMF (0.001-0.03 mg·mL$^{-1}$) through UV-Vis Spectroscopy ($\lambda$=430 nm). The polymer-protein conjugate sample was analysed by UV-Vis following freeze-drying and dissolution in DMF, with the results compared to this graph. The remainder of the aggregate solution in the dialysis membrane was kept submerged in deionized water, with samples taken out periodically over 10 days, freeze-dried, dissolved in DMF, and analysed by UV-Vis.

Cytotoxicity Tests. Human Ovarian Carcinoma A2780 cells were cultured in tissue culture flasks with Medium RPMI1640 supplemented with 10% foetal bovine serum at 37° C. under a 5% CO$_2$ atmosphere. After reaching confluency, cells were collected from the flasks with Trypsin/EDTA treatment. The cell suspension was then seeded into a 96-well cell culture plate at a cell density of 40,000 cells·mL$^{-1}$, 200 After incubation for one day, the cell in the plate was subsequently used for cytotoxicity testing. This involved firstly sterilising the micelles by UV irradiation for 1 hour, and serially diluting by half the solution with sterile water. The medium in the cell culture plate was discarded and replaced with 100 μL of fresh twice-concentrated RPMI1640 medium and the cells were incubated with the micelles for 72 hours. The cell viability was then investigated first by addition of cold TCA. The culture medium was discarded and 100 μL of 10% TCA was added to each well, followed by incubation of the plates for 30 min at 4° C. The supernatant was discarded and the plates washed 5 times with water and air-dried. 100 μL of SRB solution 0.4% (w/v) in 1% acetic acid was added to each well, and the plates incubated for 15 minutes at room temperature. After staining, the unbound dye was removed by washing 5 times with 1% acetic acid and the plates air-dried. Bound stains were solubilised with 200 μL 10 mM Tris Buffer and absorbance was measured on a Bio-Rad BenchMark microplate reader ($\lambda$=490 nm), with data analysed and plotted.

Results and Discussion

Synthesis of Protected Maleimide CPADB RAFT Agent.

The procedure described above resulted in the grafting of a protected maleimide endgroup to regular CPADB RAFT agent. The furan used in one of the reactions acted to protect the maleimide functionality to increase its compatibility in radical polymerisation processes later on in the work. Without this protection the direct use of a maleimide agent would have most likely led to branching during polymerisation steps. The furan Diers-Alder reaction is reversible, allowing the recovery of the desired maleimide moiety post-polymerisation.

It was in these steps that the true value of RAFT polymerisation to this research was revealed, through the ability to fine-tune RAFT agent functionalities present at the α-end (or ω-end in some cases) for further reaction with a range of important molecules. In the case of this work, such an important molecule was Bovine Serum Albumin through thiol-ene click chemistry with the deprotected maleimide endgroup of the α-end-functionalised RAFT polymer. FIG. 1 shows the reaction equation to form the RAFT agent used in the reaction Polymerisation and Deprotection of Methyl Methacrylate with Protected Maleimide RAFT Agent.

PMMA was primarily chosen as the suitable hydrophobic block due to its high stability with the specific chosen RAFT agent. Recent studies have investigated the effect of hydrophobic block length on polymer-protein micelle size, and concluded that cores below 8000 Da produced Average Number Distributions less than 100 nm as measured by DLS (dynamic light scattering). This was used as the basis for creating PMMA polymers of about 3000 Da and 5000 Da chain length to be used for a majority of investigations in this research in order to attempt to form aggregates well-below this 100 nm cut-off to avoid uptake by the Mononuclear Phagocyte System.

The resulting polymer chains contained a thiocarbonylthio moiety. Concerns regarding the potential toxicity of RAFT agents have been addressed in several studies showing that the toxicity can be neglected. GPC analysis of the polymers showed narrow unimodal peaks and PDI values of 1.31 and 1.26 for the PMMA-3000 and PMMA-5000 chains respectively, as expected by controlled radical RAFT polymerisation. Conversion of monomer to polymer was determined by integrating the area under the monomer and polymer peaks at 6.3 and 5.7 ppm by $^1$H-NMR Spectroscopy, yielding 78% and 64% for the PMMA-3000 and PMMA-5000 chains respectively.

Figure 2:
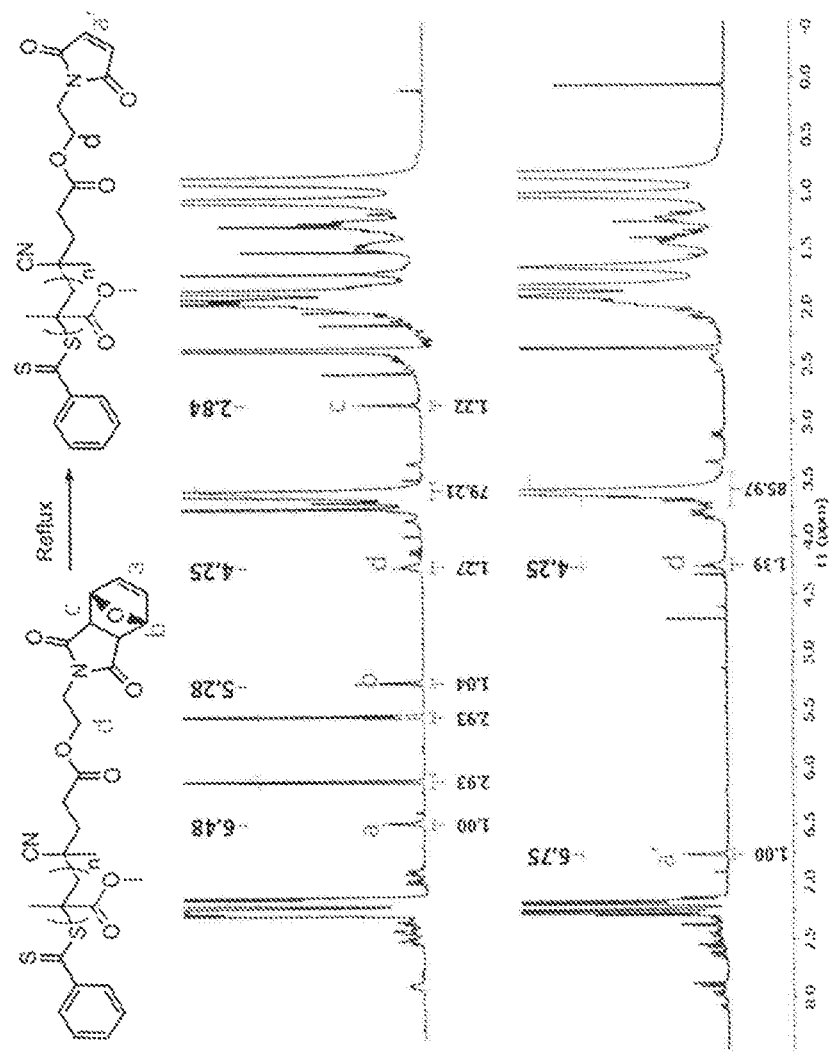
FIG. 2 shows $^1$H-NMR Spectra of crude PMMA (top) and deprotected PMMA (bottom). The removal of the peaks at 5.77 and 6.36 ppm and the appearance of the peak at 6.76 ppm indicate successful deprotection of the maleimide end-group.

Deprotection of the maleimide group attached to the polymer chains was only successful after 24 hours reflux in toluene tha. The success of this reversal of the Diels-Alder reaction in order to end-functionalise the polymer chains after chain extension was evidenced by disappearance of the peaks at 6.3 and 5.7 ppm and appearance of a peak near 6.7 ppm by $^1$H-NMR Spectroscopy, as shown in FIG. 2.

Conjugation of Bovine Serum Albumin to End-Functionalised PMMA Polymers and the Preparation of Polymer-Protein Micelles.

Figure 3:
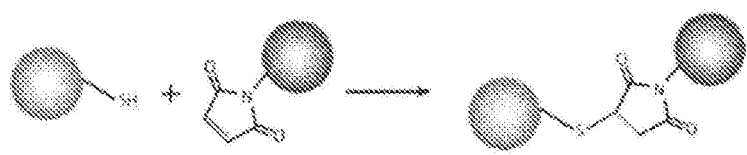
FIG. 3 shows a schematic representation of the thiol-ene conjugation of to the functionalised (deprotected) maleimide end VPMMA.

Following deprotection, the polymers were dissolved in DMSO and added dropwise very slowly to a BSA in Phosphate Buffer Solution. This mixture was left to stir for 48 hours to allow the thiol-ene click-conjugation reaction of the end-functionalised PMMA chains to the thiol groups of BSA, as shown schematically in FIG. 3. Enough polymer was added to form a final concentration of 1 mg·mL$^{-1}$.

DLS analysis was used to determine particle size of the polymer-protein aggregates after they were dialysed. Initial analyses showed Average Number Distributions around 51 nm and 121 nm for PMMA-3000 and PMMA-5000 conjugated solutions respectively, although optimisation of aggregate preparation later yielded well-defined DLS Number Distributions as low as 44 nm. It was found that using an excess of hydrophilic BSA helped to stabilise the aggregates and resulted in better particle size distributions, and investigation into the optimal ratio of solvents found that much smaller, well-defined aggregates were formed using a DMSO to Buffer ratio of 3:7.

Figure 4:
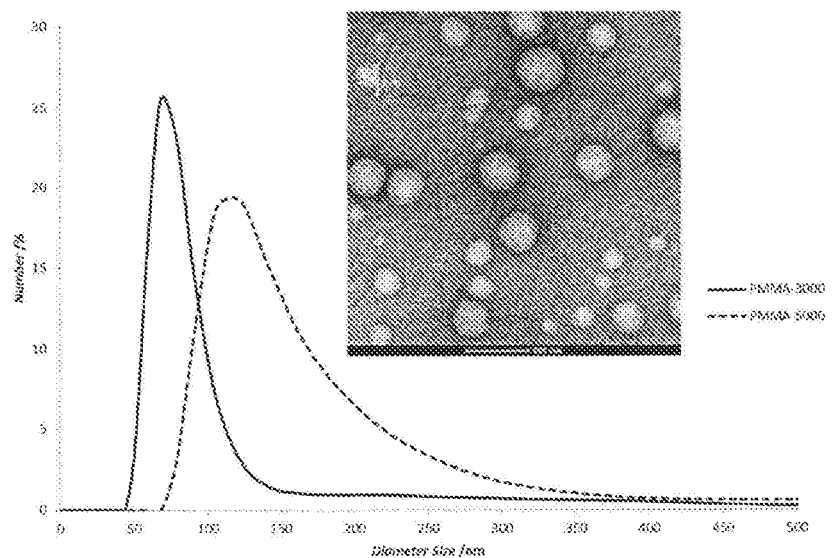
FIG. 4 shows a graph of DLS (dynamic light scattering) average number distribution of PMMA-3000-conj-BSA and PMMA-5000-conj-BSA micelles encapsulated with Curcumin in a 1:15 ratio with polymer; Inset:TEM image of the micelle solution showing aggregates below 100 nm.

On preliminary encapsulation of Curcumin drugs, DLS analysis measured Average Number distributions of 68 nm and 122 nm for PMMA-3000 and PMMA-5000 conjugated solutions respectively, with Curcumin incorporated in a 1:5 ratio with polymer. Again, optimisation of the aggregation process led to improved distributions, as low as 51 nm and 69 nm for PMMA-3000 and PMMA-5000 conjugated solutions, as shown in FIG. 4. Investigation of a number of different Curcumin to polymer ratios revealed that a molar ratio near 1:15 produced the most desirable particle sizes, as did addition of the Curcumin solution to the polymer/DMSO solution prior to conjugation (as opposed to after stirring/aggregation). TEM analysis was undertaken on the most favourably-sized distributions, as can be seen in FIG. 4 (inset), confirming the presence of micellar aggregates below 100 nm. In some cases the TEM images revealed instances of larger aggregation of particles, which was attributed to solution-drying on TEM grids prior to analysis, or the instability of protein over longer periods of time.

Figure 5:
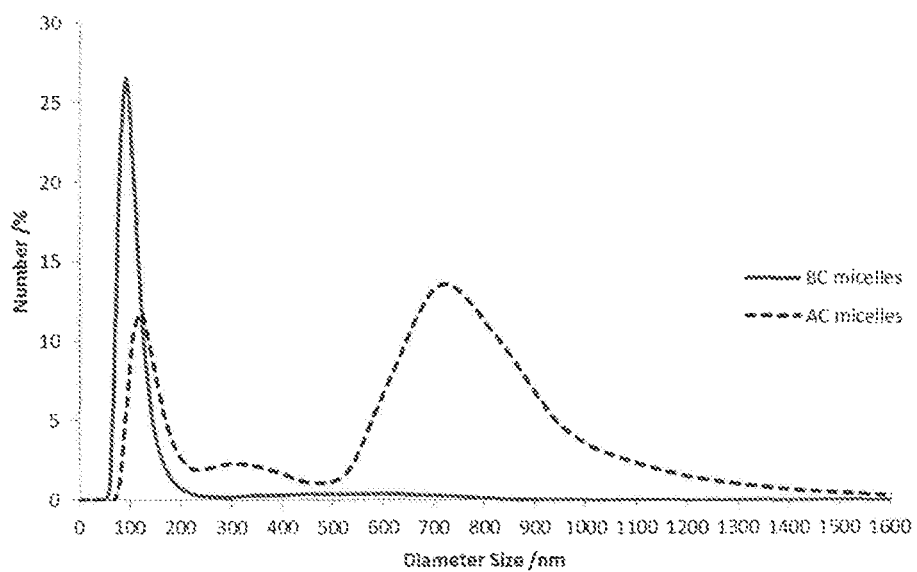
FIG. 5 shows a graph of DLS mean number distribution of Curcumin-encapsulated micelles with Curcumin added at two different times; before conjugation of polymer to protein (BC), and after conjugation/stirring of polymer to protein (AC).

FIG. 5 shows a graph of DLS mean number distribution of Curcumin-encapsulated micelles with Curcumin added at two different times: before conjugation of polymer to protein (BC), and after conjugation/stirring of polymer to protein (AC). It is clear that adding Curcumin with the polymer/DMSO mixture before conjugation produces much more well-defined, smaller sized aggregates.

Determination of Curcumin Encapsulation Efficiency and Drug Release Rate.

After the formation of polymer-protein Curcumin carrying micelles of a desirable size, there was a clear need to determine the amount of Curcumin actually encapsulated. Preliminary aggregates were loaded with Nile Red dye to act as a makeshift drug and analysed by Fluorescence Spectroscopy. After comparison to a Calibration curve established from analysis of Nile Red concentrations dissolved in DMSO solvent, the intensity was backcalculated to yield a 30.4% encapsulation efficiency.

A linear Calibration Curve was then established for Curcumin dissolved in DMF. Loaded with a 1:15 Curcumin to polymer molar ratio, a polymer-protein micelle solution from each of the two deprotected polymer chains was prepared. Small samples were taken from the two solutions following dialysis, freeze-dried, dissolved in DMF, and analysed by UV-Vis Spectroscopy. The Calibration Curve was used to calculate the concentrations of Curcumin in DMF from their absorbance results, and back-calculating gave the concentration in the original solution. A 53.7% Curcumin encapsulation efficiency was yielded from this method for PMMA-3000 conjugated aggregates and an even better 64.1% efficiency was achieved for PMMA-5000 aggregates. The higher efficiencies of Curcumin drugs over Nile Red drugs are attributed to a better compatibility with PMMA.

Figure 6:
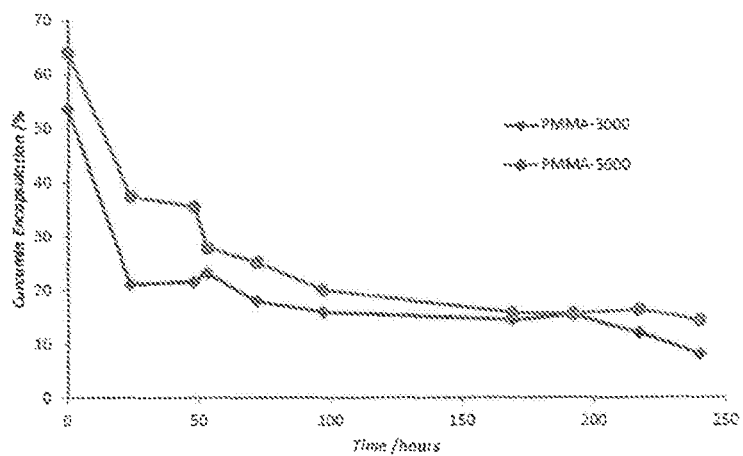
FIG. 6 shows a graph of Curcumin drug encapsulation within PMMA-3000-BSA and PMMA-5000-BSA micelles over a ten day period (1:5 Curcumin to polymer ratio), analysed by UV-Vis spectroscopy.

The remainder of the aggregate solutions were kept in dialysis membranes submerged in deionised water, and samples were taken of each at pre-determined time intervals to measure the drug release rate of Curcumin. The samples were freeze-dried and dissolved in DMF, and likewise analysed by UV-Vis, with their concentrations backcalculated from absorbance measurements. Samples were taken at 24, 48, 53, 72, 97, 169, 192, 217 and 240 hours, and the resulting decline in Curcumin encapsulation over a period of 10 days is shown in FIG. 6.

It can be seen that both samples experience the most drug release in the first 24-48 hours, with the PMMA-3000 conjugated sample dropping significantly from 53% to about 21% encapsulation, and the PMMA-5000 sample dropping from 64% to 28%. Both samples mostly plateau after this point for the next 7 or 8 days with about 8 and 14% final encapsulation respectively, appearing to almost reach a steady state with the surrounding environment.

Cytotoxicity Tests.

Following characterisation of the micelle system formed and showing it could effectively encapsulate and release Curcumin over time, the overall toxicity of the drug carriers on a cell line was then tested. The cytotoxicity study dosed Human Ovarian Carcinoma Cells with PMMA-3000 and PMMA-5000 conjugated solutions loaded with Curcumin in a 1:15 molar ratio with Polymer and a 1 mg·mL$^{-1}$ final polymer concentration.

Figure 7:
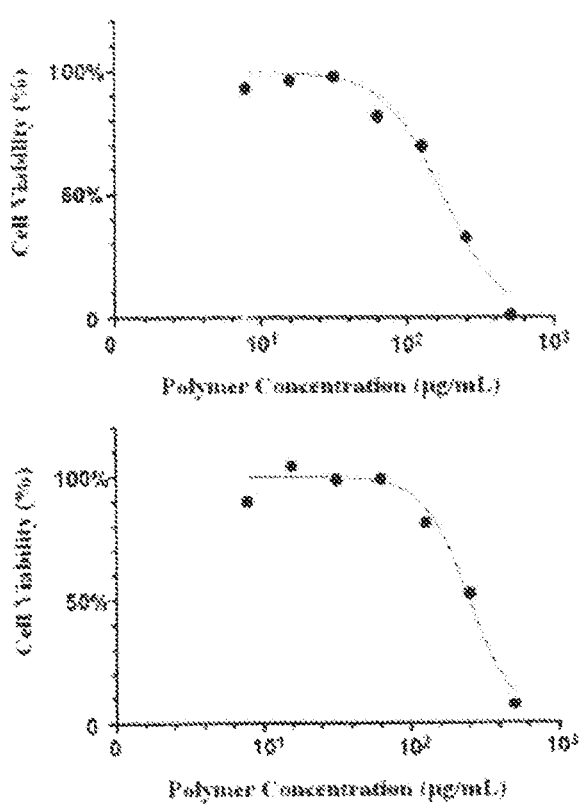
FIG. 7 shows graphs of cytotoxicity results for PMMA-3000-cnj-BSA micelles (top) and PMMA-5000-cnj-BSA micelles (bottom) encapsulated with Curcumin in a 1:15 molar ratio with polymer. IC50 (top)=248.31 $\mu g \cdot mL^{-1}$ for polymer, equivalent to 2.17 $\mu g \cdot mL^{-1}$ for Curcumin: IC50 (bottom)=174.58 $\mu g \cdot mL^{-1}$ for polymer, equivalent to 1.17 $\mu g \cdot mL^{-1}$ for Curcumin.

The results of the cytotoxicity study are shown in FIG. 7, yielding IC50 values, once converted from polymer concentrations to equivalent Curcumin concentrations, of 5.88 µM and 3.16 µM for PMMA-3000 and PMMA-5000 solutions respectively. These low values mean that the polymer-protein aggregates require Curcumin only 59% and 32% as concentrated as free Curcumin to bring about 50% cell death by comparison to even the most effective free Curcumin study results (10 µM), meaning that the drug is much more active and effective within the carriers.

Conclusion

In this Experiment, the novel production of polymer-protein amphiphiles and their potential as Curcumin drug carriers was evaluated. From the synthesis of a tailored end-functionalised RAFT agent, protected maleimide-terminated poly(methyl methacrylate) chains were extended and successfully conjugated to Bovine Serum Albumin proteins following the deprotection of the maleimide moiety via thiol-ene click chemistry. These amphiphiles were self-assembled in water to form favourably-sized micelles as low as 44 nm in diameter, verified by Dynamic Light Scattering and Transmission Electron Microscopy. On encapsulation of hydrophobic Curcumin drugs inside the hydrophobic cores, aggregation was similarly confirmed, with well-defined particles around 60 nm in diameter. It was found that better aggregation and particle size was achieved in an excess of albumin, a 3:7 DMSO to buffer ratio, and addition of Curcumin to polymer solution prior to conjugation. To then test the efficacy of the aggregates, Ultraviolet-Visible Spectroscopy was utilised to reveal an approximately 60% Curcumin encapsulation efficiency within the drug-carriers, and subsequent analysis of drug release rates revealed approximately 70% of the newly encapsulated Curcumin was released within 48 hours. Cytotoxicity studies then revealed the much higher activity and effectiveness of Curcumin within drug carriers, requiring as little as 32% of the concentration of free Curcumin required to inhibit cell-death by 50%. The development of these delivery systems is therefore crucial to the effectiveness of anti-carcinogenic drugs, with protein-polymer micellisation using functionalised RAFT polymerisation clearly a promising avenue of research to overcome issues in effective targeted anti-cancer drug delivery.

Example 2

Polymer-BSA Conjugate for the Facilitated Transport of Macromolecular Platinum Drugs An attractive target available for conjugation of a drug to bovine serum albumin (BSA) is the free thiol functionality derived from the amino acid cysteine (cyteine-34). Approximately 70% of circulating albumin in the blood stream contains this accessible cyteines-34. Cysteine-34 is located in a hydrophobic depression approximately 10-12 Å below the surface of the protein, A disadvantage with this approach is that usually only one drug molecule can be loaded per albumin molecule.

Figure 8:
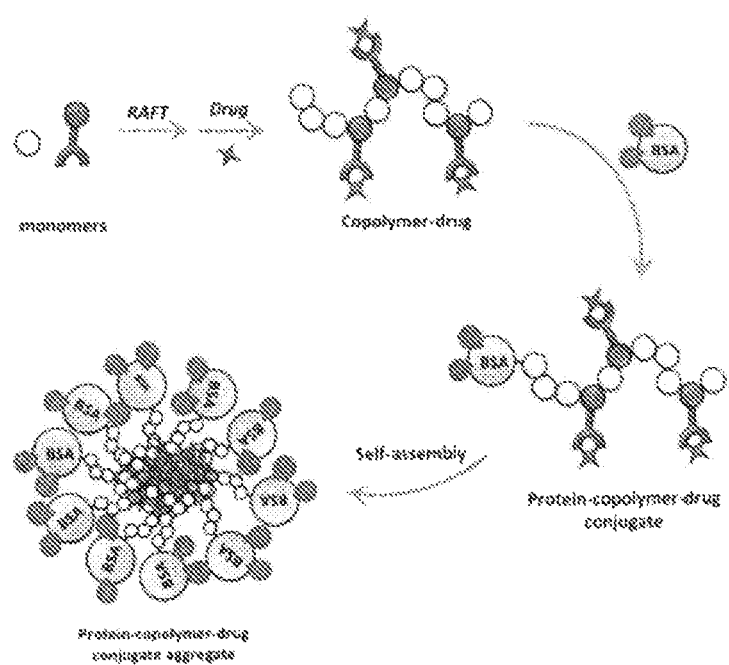
FIG. 8 shows a scheme illustrating one embodiment of production of the amphiphile assemblies of the invention.

An alternative method, which is the focus of this Example, is the formation of polymer-protein conjugates. FIG. 8 shows a schematic view of the synthesis of micelles according to this example. In summary, RAFT polymerisation followed by complexation with a suitable drug provides drug-polymer conjugates. These are then conjugated to BSA and allowed to self-assemble to form the micelles.

Maleimides are an excellent functional group for chemical attachment of polymers to proteins. Maleimides can also function as monomers during radical polymerization, thus the protection of maleimide to shield the moiety during polymerization and side reactions is important. Polymerization processes such ATRP and RAFT give well-control polymerisation processes which give rise to a narrow molecular weight distribution and afford control over the chemical structure and molecular weights. These polymerization methods can be used to design maleimide terminated ATRP initiators and maleimide-terminated RAFT agents to give rise to polymer-protein conjugates with reactive groups for protein attachment on the polymer chain-ends.

In this Example, a protein-polymer conjugate with platinum drugs was synthesised and the cytotoxicty was investigated. A maleimide-RAFT agent derived from CPADB was synthesised to obtain a maleimide-terminated statistical copolymer of PHPMA and acrylate with platinum conjugation sites. Characterisation was carried out using NMR in d-CDCl$_3$ and DMSO. Quantification of platinum content on the copolymer was determined using TGA. Due to availability of free thiol on the cysteine-34, BSA was used as a model protein for protein conjugation. A fluorescein isothiocyanate (FITC) labelled BSA (BSA-FITC) was synthesised and conjugated to the copolymer via thiol-maleimide reaction in PBS buffer. BSA quantification was carried out using UV-Vis, fluorescence spectroscopy and sodium dodecyl sulphate-polyacrylamide gel electrophoresis (SDS PAGE).

Experimental

Materials

The following chemicals are given below and used as received unless stated otherwise. N-(2-Hydroxypropyl)methacrylamide (HPMA, Sigma), acryloyl chloride (97%, Fluka), triethylamine (Et$_3$N, 99.5%, Sigma-Aldrich), DCC (Sigma), DMAP (Sigma), N,N-dimethyl acetamide (DMAc; Aldrich, 99.9%), hydrochloric acid (HCl, 32%, Univar) dimethyl sulfoxide (DMSO; Ajax, 98.9%), dimethylformaldehyde (DMF; Aldrich), diethyl ether (Univar), petroleum spirit (Aldrich), tetrahydrofuran (THF) and methanol were used without any further purification. 2,2'-Azobisisobutyronitrile (AIBN) was dissolved and recrystallized from methanol Protected Maleimide CPADB RAFT agent 4-(2-hydroxy-ethyl)-10-oxa-4-aza-tricyclo[5.2.1.02,6]-dec-8-ene-3,5-dione was synthesised as described in Example 1.

Analysis $^1$H-NMR spectra were acquired to characterised compounds using CDCl$_3$ or d-DMSO with a 300 MHz spectrometer. Thermogravimetric analysis (TGA) was carried out using TG5000 to quantify the amount of platinum conjugated to the copolymers. The sample (≤5 mg) was placed on a thermo-balance and heated from room temperature to 600° C. at 20° C./min, and held for an isothermal period of 60 minutes under nitrogen atmosphere. Diameter size of copolymers in 0.1M PBS buffer pH 7.0 was measured using a Malvern dynamic light scattering instrument (DLS) in a disposable plastic cuvette (1 cm path length). Fluorescence measurements were performed on Agilent Cary Eclipse Fluorescence Spectrometer using a 1 cm quartz cuvette. Fluorescence spectra were recorded between 400-800 nm at $\lambda_{ex}$=495 nm, $\lambda_{em}$=520 nm with entrance and exit slit width of 5 mm. SDS-PAGE was performed using standard techniques using a premixed electrophoresis buffer which contains 25 mM Tris, 192 mM glycine and 0.1% SDS (Tris/Glycine/SDS buffer) to determine the conjugation efficiency between the BSA-FITC and the copolymer. Samples were prepared for electrophoresis without the use of a reducing agent. The samples were mixed with bromophenol blue (0.01% w/v) solution as the marker. The samples were resolved through a 10% polyacrylamide gel which was performed using a BioRad Mini-Protean II electrophoresis setup at a constant voltage (150 V). The samples were stained using Colloidal Blue Coomassie G-250 (Bio-Rad), and left overnight. Gel images were recorded using a Bio-Rad GS-800 calibrated densitometer. Native BSA was used as a control.

Synthesis and Procedures

Synthesis of N-BOC Protected 1,3-Diaminopropanol Acrylate Monomer (DAP-BOC-AC):

DAP-BOC (6.00 g, 20.6 mmol) and Et3N (3.00 mL, 21.7 mmol) was dissolved in anhydrous THF (20.00 mL) and purged with nitrogen for 15 minutes. A solution of acryloyl chloride (2.20 mL, 22.6 mmol) in anhydrous THF (20 mL) was then added to the reaction dropwise with constant stirring and cooled in an ice bath at 0° C. After the addition of acryloyl chloride, the reaction mixture was left to stir for 1 hour and then removed from the ice bath to stir under room temperature for 24 hours. The precipitated Et$_3$N salt was filtered off and washed with THF and the solvent in the filtrate was evaporated under reduced pressure on a rotary evaporator producing a yellow liquid product. The liquid was stored in the fridge overnight yielding white crystals. The crystals were collected by filtration and recrystallised in THF. (Yield: 62%)

RAFT Polymerisation of HPMA and DAP-BOC-AC Using Protected Maleimide Terminated RAFT Agent, P(HPMA-co-Ac-DAP-BOC):

N-(2-Hydroxypropyl) methacrylamide (0.093 g, 0.68 mmol), Ac-DAP-BOC (4) (0.1 g, 0.29 mmol), MCPADB (3) (15.3 mg, 0.033 mmol) and AIBN (1.6 mg, 0.0098 mmol) were dissolved in 1 mL of DMSO. The reaction mixture was purged with nitrogen for 30 minutes. The reaction mixtures were then immersed in an oil bath at 70° C. for 8 hours. The polymerization was terminated by placing the samples in an ice bath for 5 minutes. The polymer was purified three times by dissolution in additional acetone and then precipitation in diethyl ether. After centrifugation (7000 rpm for 15 min), the polymer was dried under reduced pressure at room temperature. The samples were stored in a freezer prior to any modifications. The conversions are calculated from the reaction mixture via $^1$H NMR.

Removal of BOC Protective Group:

The polymer was dissolved in 1 mL DMF, followed by 3 drops of concentrated hydrochloric acid 32 (w/v %). The reaction was left to stir over night at r.t and the polymer was purified by precipitation in diethyl ether. After centrifugation (7000 rpm for 15 min), the polymer was dried under reduced pressure at room temperature.

Conjugation of Platinum-DMSO Complex onto Copolymers:

The copolymer with active conjugation sites was dissolved in DMF and 1 eq. of Pt(DMSO)$_2$Cl$_2$ complex was added. The reaction was stirred for 24 hours at room temperature. Lithium chloride (5 mol eq.) was added into the solution and reacted for another 6 hours at 80° C. The reaction mixture was cooled to ambient temperature and purified via dialysis against deionised water (DI) using MWCO 3500 over 2 days. After freeze-drying, a brown solid of Pt-conjugated copolymers was obtained. TGA was used to determine the platinum content on the copolymer.

Cleavage of Furan Protection Groups on the Maleimide Copolymer:

The deprotection of furan protection group was performed in situ during the platinum conjugation reaction during heating at 80° C. for 6 hours. The reaction mixture was cooled and purified as the above method.

Synthesis of BSA-FITC Polymer Conjugate

Synthesis of BSA-FITC:

A 2 mg/ml BSA solution was made using 100 mg BSA in 50 ml of 0.1M NaCO$_3$ buffer. A 1 mg/ml FITC solution was made using 2.5 mg of FITC in 2.5 ml DMSO. The FITC solution was added into the BSA solution and stirred for 24 hours. The mixture was dialysed against 0.1 M PBS buffer for 3 days to obtain a yellow solution. The concentration of BSA used and the molar ratio of BSA to FITC were determined using UV-Vis.

Conjugation of BSA-FITC and Maleimide-Copolymer:

Platinum conjugated copolymer (0.7 mg, 0.04 µmol, 31% end-group fidelity) was dissolved in 0.2 mL of DMSO and was added dropwise into a solution of BSA-FITC (0.7 mg, 0.01 µmol) in 4 mL of PBS buffer (0.1M, pH 7.0) under stirring. The mixture was stirred for 48 hours at room temperature and subsequently dialysed against 0.1M PBS buffer for 24 hours. After dialysis, the supernatant containing BSA-polymer conjugate was finally collected and analysed by fluorescence spectroscopy, SDS PAGE and DLS.

Cell Culture

The OVCAR-3 cell line were grown as monolayer cultures in cell culture flasks using Roswell Park Memorial Institute (RPMI-1640) media containing 10% Foetal Bovine Serum (FBS) and 5 mL of L-Glutamine-Penicillin-Streptomycin solution (with 200 mM L-glutamine, 10,000 units penicillin and 10 mg/mL streptomycin in 0.9% NaCl, sterile-filtered). Penicillin was added as an antibiotic. Cell cultures were grown in a humidified atmosphere at 5% CO$_2$ at 37° C. The medium was routinely changed every 3 days. For subculture experiments, cells grown in monolayer were released by washing with PBS (10 mL) and then treatment with 0.05% of trypsin/EDTA.

In Vitro Cell Proliferation Assay

The cytotoxicity of the polymer, platinum incorporated polymer and BSA-conjugated micelles were measured by a standard sulforhodamine B colorimetric proliferation assay (SRB assay). The SRB assay was established by the U.S. National Cancer Institute for rapid, sensitive, and inexpensive screening of antitumor drugs in microtiter plates. For the cytotoxicity assay, 100 µL of OVCAR-3 cells were seeded in 96-well microtiter plates at a density of 5000 cells per well, and were allowed to adhere overnight. The growth medium was replaced with fresh medium (200 µL) containing various concentration of test material. The cells were incubated for a further 72 hours.

The culture medium was discarded and the live cells were fixed with 200 µL of trichloroacetic acid 10% w/v (TCA) for 1 h at 4° C. before washing five times with tap water. After removal of water the TCA-fixed cells were stained with 0.4% (w/vol) SRB dye dissolved in 1% acetic acid for 30 minutes. The unbounded dye was then removed by washing five times with 1% acetic acid. The plates were left to air dry overnight followed by the addition of 100 μl, of 10 mM unbuffered Tris base to each well to dissolve bounded dye. The absorbance was determined using a multiwell scanning spectrophotometer at a wavelength of 570 nm. Dose-response curves were plotted (values expressed as percentage of control (non-treated cells were used as controls). The optical density (OD) was used to calculate cell viability. IC50 inhibitory concentrations were estimated by regression analysis.

Cell viability(%)=($OD_{570,sample}$−$OD_{570,blank}$)/
($OD_{570,control}$−$OD_{570,blank}$)×100

BSA-FITC Conjugation

Figure 9:
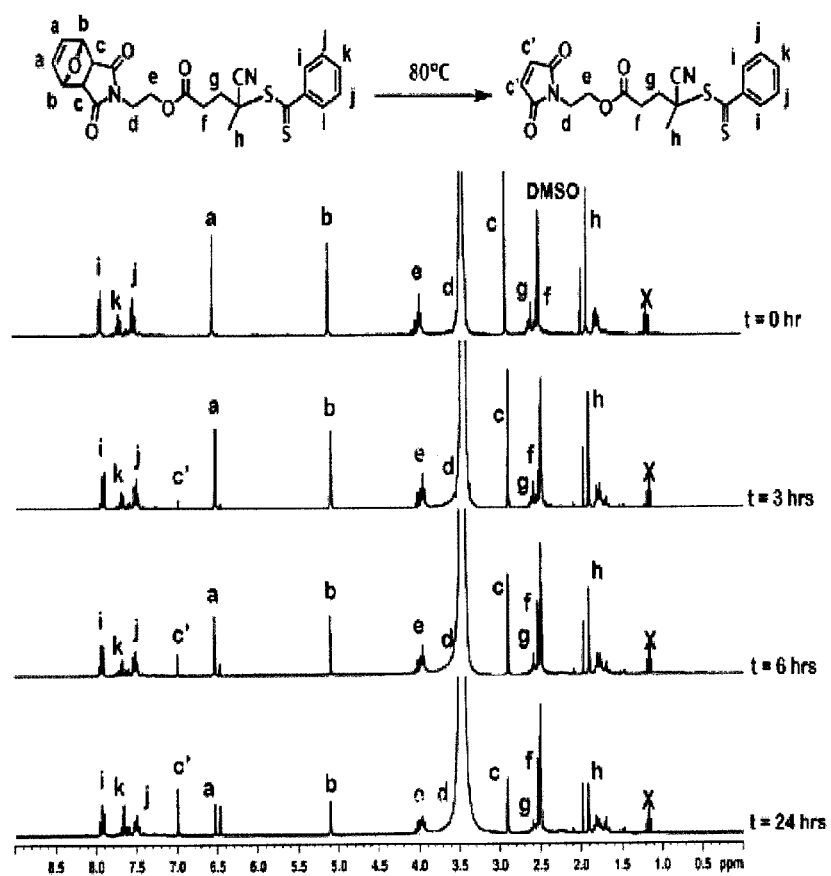
FIG. 9 shows a series of $^1$H nmr spectra illustrating deprotection of maleimide-RAFT at 80° C. in DMSO.

BSA conjugation was implemented using the readily available free-cysteine (Cys-34) residue of the bovine serum albumin (BSA) via maleimide-thiol reaction. To allow conjugation of BSA to occur, the furan protected maleimide-RAFT copolymer was deprotected by heating to result in the reactive maleimide functionality. Refluxing a solution of the compound in toluene is typically applied for deprotection. Since the platination reaction included a step where the solution was heated at 80° C. with LiCl, it was assumed that the deprotection of maleimide may also proceed at this temperature. To verify this hypothesis, a control reaction using the protected RAFT agent only was carried out in DMSO at 80° C. The reaction was followed by 1H NMR to monitor the decrease of signal a, b and c of the protecting group (FIG. 9).

Figure 10:
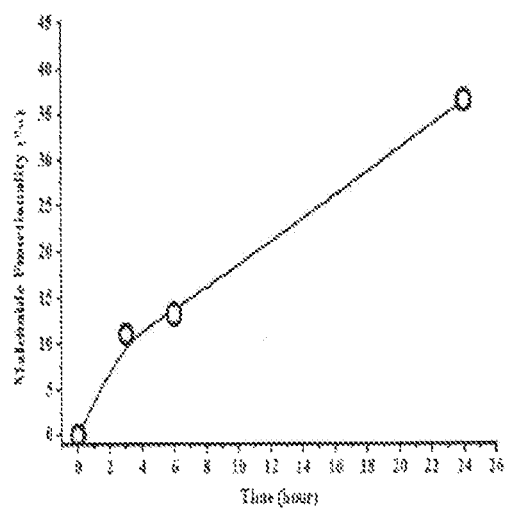
FIG. 10 shows a graph of the amount of deprotected maleimide functionalities vs time at 80° C.

The characteristic signal of the resulting double bond (signal c') at 7.0 ppm increased over time but did not progress to full conversion. FIG. 10 shows the progress of the deprotection versus time. After 6 hours of heating at 80° C., only 13% of maleimide was formed. However, deprotection of the polymer under these conditions was found to be more efficient. Deprotection of P(HPMA13-co-[(AC-DAP)9-Pt8]) resulted in higher conversions after 6 hours of heating at 80° C. as observed using 1H NMR analysis. The copolymer was dissolved in DMF and locked with d-DMSO to monitor the protected maleimide signal a at 6.6 ppm and the unprotected maleimide signal c' at 7.0 ppm. From Table 1, it was calculated that approximately 31% of free maleimide was formed. The difference in conversion is likely due to the solvent choice and potentially the miscibility of the resulting furan and the solvent. It can be argued that removing furan by heating under reduced pressure could improve the outcome since the low boiling furan is continuously removed from the system.

TABLE 1

Maleimide conversion of P(HPMA13-co-[(AC-DAP)9-Pt8]) using 1H NMR

| Copolymer | Intg. NMR Peak a[b] | Intg. NMR Peak c[b] | Conversion (%)[c] |
|---|---|---|---|
| Unprotected Copolymer [a] | 2.000 | 0.9000 | 31 |

[a] Unprotected copolymer of P(HPMA$_{13}$-co-[(AC-DAP)$_9$-Pt$_8$]) was obtained after platination and LiCl reaction in DMF at 80° C. for 6 hours
[b] Integrations (Intg.) of 1H NMR of the pure P(HPMA$_{13}$-co-[(AC-DAP)$_9$-Pt$_8$])
[c] Calculated from100* [Intg(peak c)/2]/[Intg(peak a)/2 + Intg(peak c')/2]

Figure 11:
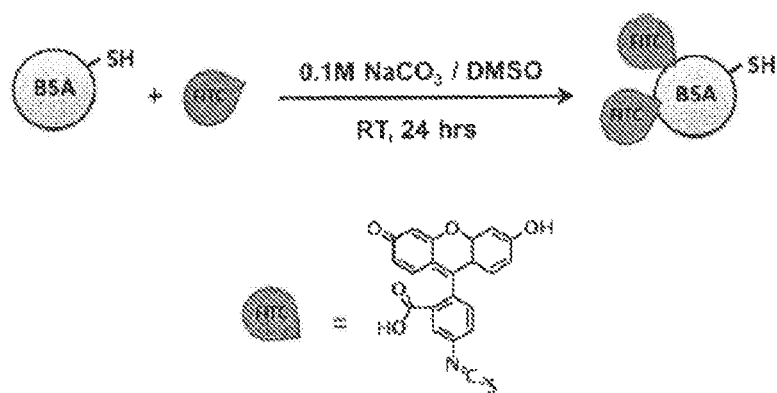
FIG. 11 shows a scheme illustrating labelling BSA using FITC (fluorescein isothiocyanate) in carbonated buffer and DMSO.

Meanwhile, BSA was labelled with a fluorescent marker, fluorescein isothiocyanate (FITC), to allow monitoring of the final product in the cell experiments. FITC provides a simple method of attachment of a fluorescent dye through isocyanate with the primary amino groups available on protein as shown in FIG. 11.

The quantity of FITC attached on a BSA was calculated as a dye/protein molar ratio. Based on the absorbance values of the native BSA and BSA-attached FITC in FIG. 12, the molar concentration of BSA and FITC can be determined individually and these concentrations can be expressed as a ratio. The UV absorbance for native BSA appears at 280 nm (solid line). With the conjugated BSA-FITC (solid with dotted line), the compound gives 2 individual absorbance values at 280 nm for BSA ($A_{280}$=0.94) and 495 nm for the FITC dye ($A_{495}$=1.54). Initially, the molarity of BSA in the solution was obtained using the equation below, $$BSA\ concentration,\ [BSA] = \frac{A_{280} - (A_{max} \times CF)}{\varepsilon} \times \text{dilution factor}$$

where $A_{max}$ is the absorbance at the wavelength maximum for FITC in solution, ε is the BSA molar extinction coefficient (43824 $M^{-1}$ CF is the correction factor which is adjusts for the amount of absorbance at 280 nm caused by FITC (0.3000).

Thus, from the equation, it can be determined that the concentration of BSA in PBS solution used is 2.54 $10^{-5}$ M. The degree of labelling moles of FITC per moles of BSA was calculated to be 2.1, using the equation below, $$\frac{\text{moles of } FITC}{\text{moles of } BSA} = \frac{A_{max}}{\varepsilon' \times [BSA]} \times \text{dilution factor}$$

where ε' is the molar extinction coefficient of FITC (68000 $M^{-1}$ $cm^{-1}$)

Figure 12:
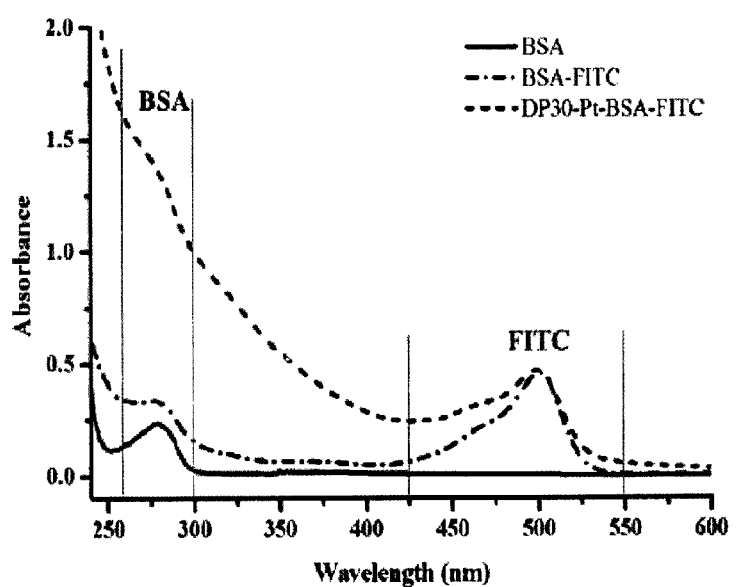
FIG. 12 shows UV absorbance of BSA, BSA-FITC and BSA-FITC conjugated copolymer-Pt.
Figure 13:
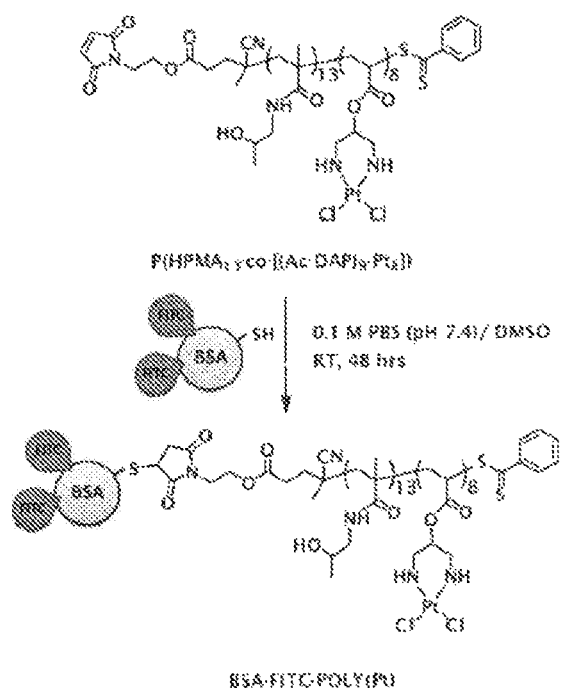
FIG. 13 shows a scheme of BSA conjugation to the polymer end chain.

It is known that conjugation of BSA can be performed using a simple reaction in PBS buffer at pH 6.5. As shown in FIG. 13, DMSO was used as a co-solvent to dissolve the copolymer. BSA was added into the copolymer solution with vigorous stirring to prevent precipitation. The conjugation reaction was proceeded for 48 hours to allow maximum conjugation. The initially, clear yellow solution was observed to turn slightly opaque over time. The reaction mixture was purified via dialysis against 0.1M PBS buffer pH 7 using MWCO 12000 dialysis membrane. Upon BSA-FIC conjugation to the copolymer, the UV-VIS spectroscopy shows an increase of absorbance after 400 nm which gives evidence of the presence of copolymers conjugated with the BSA-FITC (FIG. 12).

Figure 14:
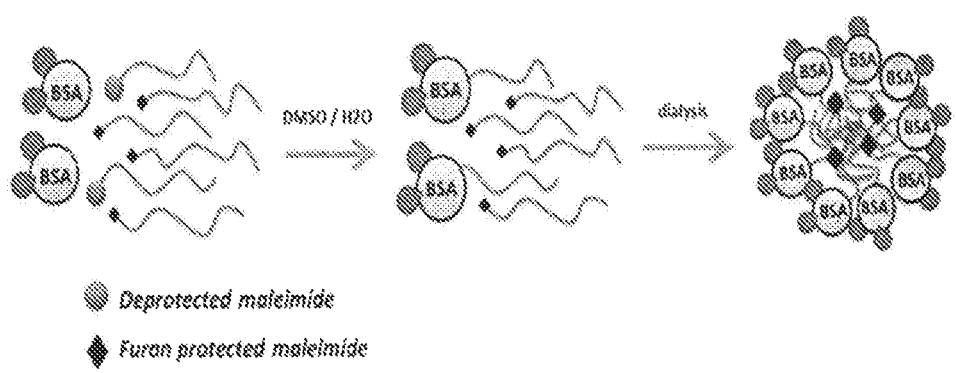
FIG. 14 shows a scheme of formation of nanoparticles coated with BSA in PBS buffer.

It should be noted here that a three times-excess of polymer is needed, taking into account that only one third of polymer has been deprotected. It was not known if dialysis against PBS buffer can remove the excess polymer since the macromolecular drug is poorly soluble in water. Upon dialysis, unreacted polymers could potentially be entrapped in the core of the core-shell nanoparticle, which is coated by a layer of albumins (FIG. 14). Therefore, analysis was conducted to determine the exact ratio between polymer and albumin in the purified sample. This was achieved using fluorescence spectroscopy and inductively coupled plasma optical emission spectroscopy (ICP-OES). First, the concentration of BSA-FITC conjugated to the copolymer in the solution was determined using fluorescence spectroscopy. BSA-FITC was diluted with 0.1 M PBS buffer to a concentration of 0.08 mg/ml which lead to an intensity of 578.82. The solution containing the BSA-FITC-P(HPMA$_{13}$-co-RAC-DAP)$_9$-Pt$_8$]) with polymer concentration of 0.049 mg/ml resulted in an emission intensity of 760.30. From these numbers, the relative concentration of BSA-FITC attached on the BSA-FITC-P(HPMA$_{13}$-co-[(AC-DAP)9-Pt$_8$]) was calculated to be 0.11 mg/ml. Considering that three-times the molar ratio of polymer was used for the conjugation between polymer and BSA, (which coincidentally is equivalent to the same mass as BSA) the solution of BSA-FITC-P(HPMA$_{13}$-co-RAC-DAP)$_9$-Pt$_8$]) would have of a copolymer concentration of 0.11 mg/ml, which is equivalent to a Pt concentration of 0.0341 mg/ml. If dialysis did not remove any excess polymer, ICP-OES analysis should result in a similar concentration. In contrast, full removal of excess polymer and the successful conjugation in a 1:1 ratio between polymer and BSA should lead to a solution with a platinum concentration of 0.0121 mg/ml. ICP-OES revealed a platinum concentration of 0.0134 mg/ml for the BSA-FITC-P(HPMA$_{13}$-co-[(AC-DAP)$_9$-Pt$_8$]), which is only slightly higher than the theoretically calculated value for a 1:1 complex. The platinum concentration therefore suggests that almost all unbound polymer was removed during the dialysis process.

Figure 15:
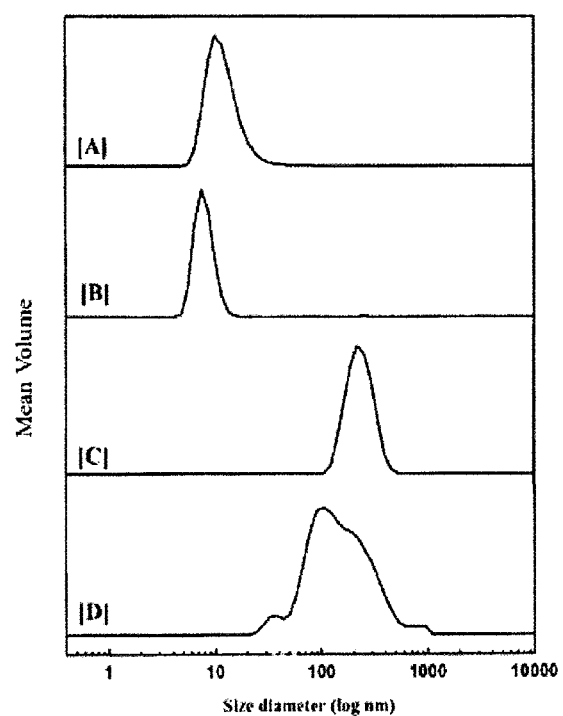
FIG. 15 shows DLS measurement of size according to volume in PBS buffer pH7.0 of P(HPMA$_{13}$-co-[(AC-DAP)$_9$-Pt$_8$] before BSA conjugation (A and B) and after BSA conjugation (C and D).

The size and shape of the BSA conjugated copolymer in PBS solution was investigated using DLS and TEM. FIG. 15 shows the hydrodynamic diameter distributions of different samples analysed at 25° C., [A] native BSA, [B] BSA-FITC, [C] P(HPMA$_{13}$-co-[(AC-DAP)$_9$-Pt$_8$]) and [D] BSA-FITC conjugated P(HPMA$_{13}$-co-[(AC-DAP)9-Pts]). The BSA and BSA-FITC exist as unimers in PBS buffer. The copolymer prior to conjugation gives in nanoparticles of around 200 nm in diameter.

Although PHPMA is water-soluble, the presence of the platinum drug leads to an amphiphilic structure with a tendency to aggregate, resulting in a bigger diameter size. Upon conjugation with BSA-FITC, amphiphilic block copolymers are formed with a hydrophilic BSA and a rather hydrophobic polymer. It is expected that these polymers self-assemble in solution into core-shell nanoparticles. The measured sizes of all compounds are summarised in Table 2.

TABLE 2

Hydrodynamic diameter distributions of BSA conjugated copolymer in 0.1M PBS pH 7

| Sample | Conc. (mg/ml) | $D_h^{number}$ (d/nm) | PDi |
|---|---|---|---|
| BSA | 1.000 | 9.93 | 0.42 |
| BSA-FITC | 0.800 | 7.44 | 0.58 |
| P(HPMA$_{13}$-co-[(AC-DAP)$_9$-Pt$_8$])$^a$ | 0.095 | 198.6 | 0.14 |
| BSA-FITC-[P(HPMA$_{13}$-co-[(AC-DAP)$_9$-Pt$_8$])]$^b$ | 0.11$^c$ | 82.0 | 0.27 |

Figure 16:
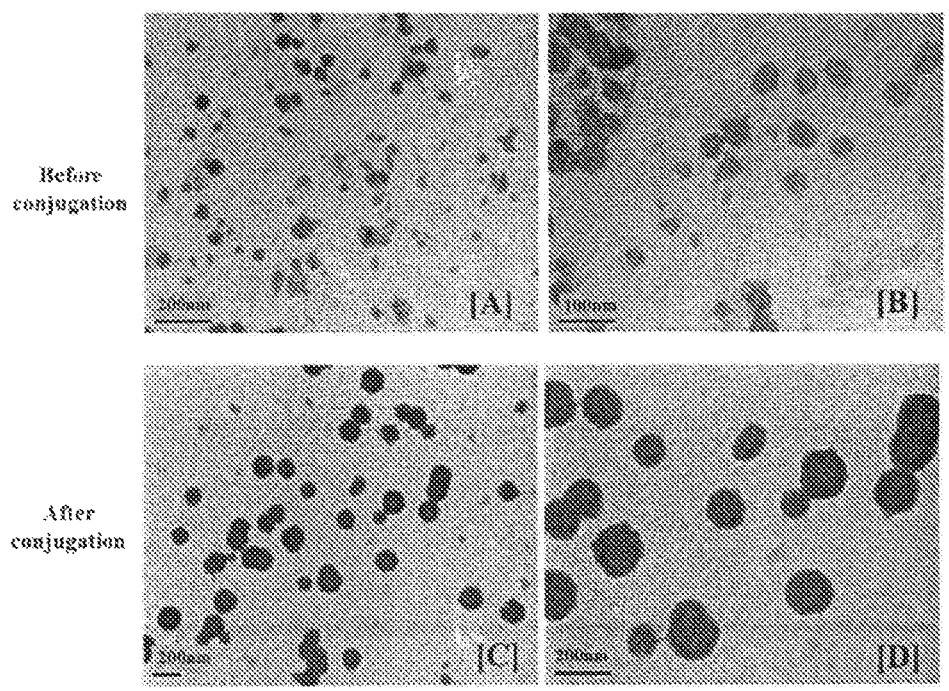
FIG. 16 shows Transmission electron microscopy (TEM) of P(HPMA$_{13}$-co-[(AC-DAP)$_9$-Ptg] before BSA conjugation (A and B) and after BSA conjugation (C and D).
Figure 17:
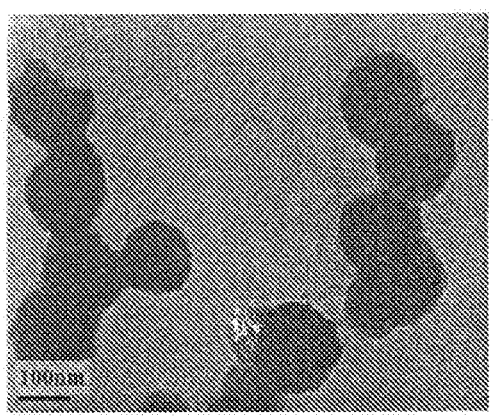
FIG. 17 shows a transmission electron micrograph of aggregates of BSA-FITC conjugated polymer.

$^a$Dissolved in DMSO and dialysis against 0.1M PBS buffer pH 7 for 24 hours
$^b$Conjugation was performed in DMSO/PBS buffer and purified via dialysis using MWCO 12000 membrane for 48 hours
$^c$Concentration of BSA-FITC conjugated to copolymer was determined via fluorescence spectrascopy Transmission electron microscopy (TEM) confirmed the presence of platinum in all samples, before and after BSA-FITC conjugation (black dots). The platinum assists the visibility of the particles without the need for staining (FIG. 16). Before BSA conjugation, the macromolecular drug aggregates in various undefined structure. Although DLS suggests a size of around 200 nm, TEM reveals the presence of smaller sizes, but also a tendency to aggregate. The particles are clearly bigger upon BSA conjugation, with the TEM and DLS size in good agreement. The polymer conjugated BSA-FITC showed a consistent spherical shape in the TEM however some of the particles expressed a tendency to aggregate between each other to form bigger particles sizes as shown in FIG. 17. This is in agreement with the DLS result where the large PDI indicates the presence of larger size distributions.

Figure 18:
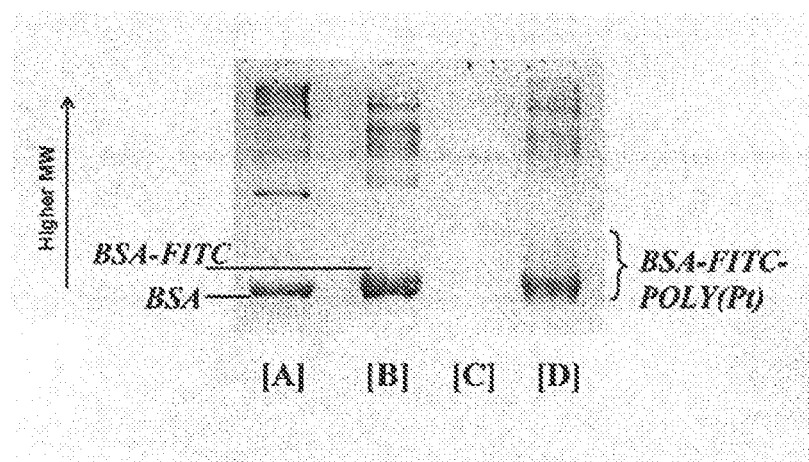
FIG. 18 shows SDS-PAGE analysis of BSA-conjugated P(HPMA13-co-[(Ac-DAP)9-Pt8). [A] Native BSA 0.1 mg/ml, [B] BSA-FITC 0.1 mg/ml, [C] P(HPMA13-co-[(Ac-DAP)9-Pt8) 0.09 mg/ml, [D] BSA-FITC-P(HPMA13-co-[(Ac-DAP)9-Pt8) 0.1 mg/ml.

Another method used to confirm the conjugation between the BSA and the copolymer was SDS-PAGE (FIG. 18). SDS-PAGE is normally used for protein separations, the basis of molecular weight. Electrophoresis was carried out using Tris/Glycine/SDS buffer on a 10% polyacrylamide gel. A commercial BSA (lane [A]) with molecular weight of 66 000 g/mol was used as a control. The synthesised BSA-FITC (lane [B]) with similar BSA concentration, but with a 2.1 molar ratio of dye, showed a slightly higher molecular weight band, suggesting that FITC is attached on the BSA. Lane [C] represents the copolymer, which is not visible via gel electrophoresis. Lane [D] indicates the band for polymer-BSA conjugate. A smeared band of the BSA-FITC-conjugated copolymer with a considerably darker band at a similar height of BSA-FITC suggests that the BSA-FITC is attached to the copolymer. Since the molecular weight of the conjugated copolymer is only 6000 g/mol, the increase in molecular weight is around 10%, resulting only in a minor effect on the SDS-PAGE.

In Vitro Cytotoxicity Activity of the Conjugate

The aim of this work was to use albumin as a better transport vehicle for delivery of the macromolecular drug. It is hypothesized flat albumin can lead to better cell-uptake and therefore to higher toxicity. The prepared BSA-conjugated polymer was therefore tested towards its activity against OVCAR-3 ovarian cancer cells. For control, the polymer aggregate based on P(HPMA13-co-[(AC-DAP)$_9$-Ptg]) was employed. The concentrations of both solutions, for platinum free copolymers and BSA-FITC-conjugated copolymers are summarised in Table 3.

TABLE 3

Copolymer and platinum concentrations of BSA-polymer conjugates

| Sample | [BSA]$^a$ (mg/ml) | [Copolymer] (mg/ml) | [Pt] (mg/ml) | [Pt] (µM) |
|---|---|---|---|---|
| P(HPMA$_{13}$-co-[(AC-DAP)$_9$-Pt$_8$]) | — | 0.095 | 0.0272$^b$ | 140 |
| BSA-FITC-[P(HPMA$_{13}$-co-[(AC-DAP)$_9$-Pt$_8$])] | 0.11 | 0.0462 | 0.0134$^c$ | 68 |

Figure 19:
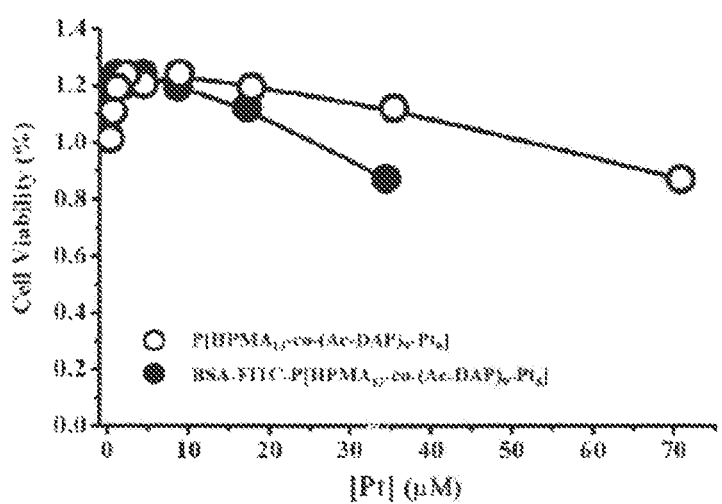
FIG. 19 shows cell viability of OVCAR-3 ovarian cancer cells for [P(HPMA13-co-[(AC-DAP)9-Pt8])] before (○) and after (●) BSA-FITC conjugation.

$^a$Concentration of BSA-FITC conjugated to copolymer was determined via fluorescence spectroscopy
$^b$Concentration of platinum was determined via thermal gravimetric analysis(TGA)
$^c$Concentration of platinum was determined via ICP-OES Both solutions were employed in an in vitro cytotoxicity test against OVCAR-3, ovarian cancer cell lines. The percentages of the cell viability of both samples are presented in FIG. 19. It should be noted that the highest concentration is lower than the concentration listed in Table 3 due to dilution. Unfortunately, even the highest concentration could not completely inhibit cell viability. However, the copolymer conjugated with BSA-FITC was clearly more toxic, confirming that albumin can enhance the delivery of the drug into the cell despite the BSA-conjugated polymer having a larger particle size than the polymer alone.

Conclusions

RAFT polymerisation was shown to be a versatile technique to design polymer-protein conjugates by modification of the R-group of the RAFT agent. Maleimide-functionalised RAFT agent was successfully used to obtain P[HPMA-co-(Ac-Dap-BOC)] with a maleimide end functionality. Platinum drugs were conjugated after removal of the BOC protecting group to yield a platination efficiency of 93%, determined by TGA analysis. Cleavage of furan-protection groups on the copolymer chain-ends was performed prior to conjugation of BSA by maleimide-thiol reaction. At 80° C. the conversions into free-maleimide groups on the copolymers were not complete (31%) and needs to be optimised further. Nevertheless, conjugation of BSA to copolymer was still attempted using a 1:1 ratio between BSA and reactive polymer, taking into account that the deprotection was not complete. With evidence from SDS-PAGE, fluorescence, ICP-OES and UV-VIS spectroscopy conjugation was confirmed to be successful although the attachment of a small polymer to BSA was barely detectable using SDS-PAGE. Cell cytotoxicity tests also gave promising results which indicate that the BSA-conjugated copolymers were more toxic than the unconjugated controls.

Example 3

This example illustrates a one-pot production method for an albumin-coated polyion complex micelle incorporating multifunctional oligonucleotide transfection vectors.

Figure 20:
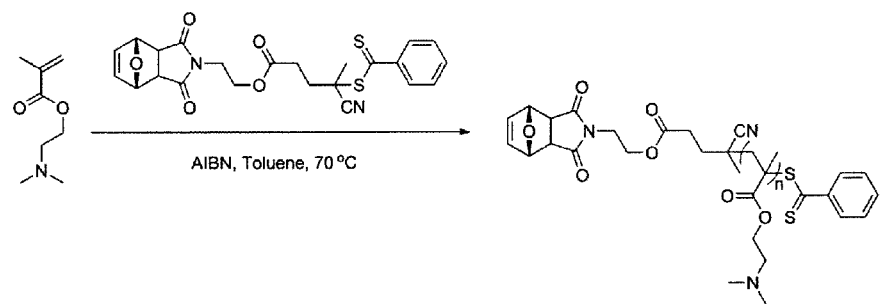
FIG. 20 shows a scheme of the synthesis of PDMAEMA.
Figure 20:
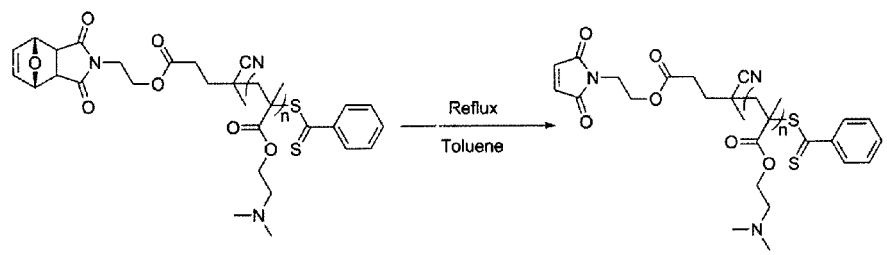
Figure 21:
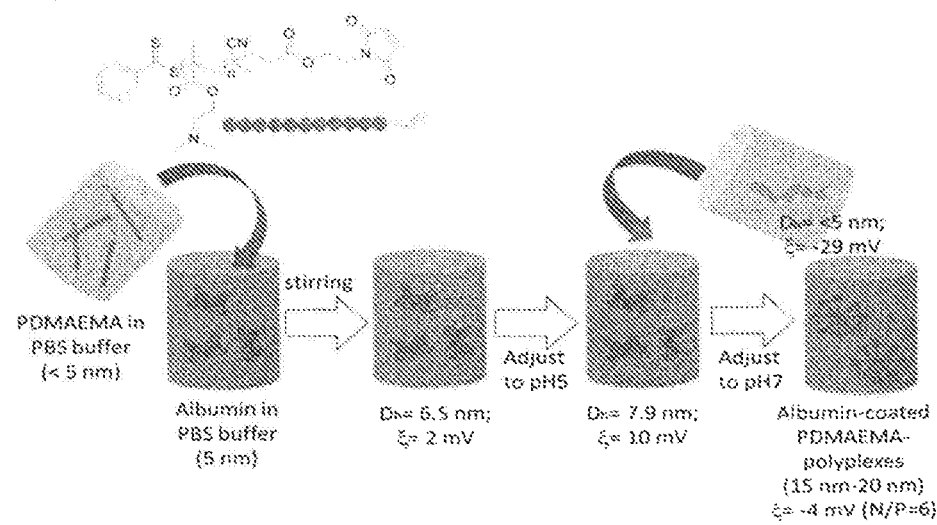
FIG. 21 shows a scheme of the synthesis of polyion complex micelles.

In general terms, dimethylaminoethylmethacrylate (DMAEMA) was synthesised using RAFT polymerisation with a protected RAFT agent. The resulting polymer was deprotected in refluxing toluene to provide a maleimide-terminated polymer. This was then dissolved in a buffer solution. The solution was combined with a buffered albumin solution and adjusted to pH 5, so as to conjugate the polymer to the albumin. Addition of ISIS 5132 (a 20-base antisense phosphorothioate oligodeoxyribonucleotide: 5'TCCCGCCTGTGACATGCATT3') resulted in formation of micelles containing the ISIS 5132. The synthesis of the polymer is illustrated in FIG. 20 and the production of micelles from the polymer and albumin is shown in FIG. 21.

The resulting micelles were then tested for uptake into cells and for cytotoxicity.

Syntheses

Synthesis of PDMAEMA Via RAFT Polymerization.

DMAEMA (14.148 g, 0.09 mol), MCPADB (0.21 g, $7.9 \times 10^{-4}$ mol), and AIBN (0.0374 g, $2.28 \times 10^{-4}$ mol) were combined with methanol to achieve a concentration of 1.5 mol/ml. The ratio was [monomer]:[RAFT agent]: [Initiator]=120:1:0.2. The reaction mixture was divided equally into 3 vials. After sealing the reaction flasks, the mixture was purged with nitrogen for 1 h at 0° C. Four of the flasks were immersed in an oil bath at 70° C., and samples were taken over a period of 24 h. The vials were removed at 3, 5 and 7 h. Polymerization was terminated by placing the sample bottles in an ice bath for 5 mM. The same procedure was also used to prepare polymers with longer polymer chains at the ratio of [DMAEMA]:[MCPADB]: [Initiator]=350:1:0.2. The polymer was purified by precipitation in cyclohexane and finally dried under reduced pressure. The conversion and the theoretical molecular weight (Mn) was determined $^1$H NMR (CDCl$_3$). The polydispersity index ($M_w/M_n$) was measured by gel permeation chromatography (GPC) using DMAc as solvent. Results are shown in Table 4.

TABLE 4

RAFT polymerization of PDMAEMA

| Sample | [M]:[RAFT]:[I] | Time (h) | Con. (%)$^a$ | $M_n$, theo (g·mol$^{-1}$) | GPC$^b$ Mw/Mn | $M_n$, after deprotection |
|---|---|---|---|---|---|---|
| 1 | 120:1:0.1 | 3 | 42.6 | 8528 | 1.14 | 8443 |
| 2 | 120:1:0.1 | 5 | 55.7 | 10518 | 1.17 | 10434 |
| 3 | 120:1:0.1 | 7 | 74.5 | 14550 | 1.16 | 14465 |
| 4 | 350:1:0.1 | 5 | 38.7 | 21793 | 1.15 | 21709 |
| 5 | 350:1:0.1 | 16 | 84.4 | 46984 | 1.17 | 46900 |

$^a$Obtained from 1H NMR analysis;
$^b$Determined from DMAc GPC (relative to PS standards).

Deprotection of End-Functionalised PDMAEMA 1.3 g polymer was dissolved in 50 mL toluene and the solution was brought to reflux at 110° C. for 7 hours. Therefore, the Diels-Alder protection reaction of the maleimide moiety attached to the RAFT agent on the ends of the polymer chains would be reversed. The solvent was evaporated and further dried with a Schlenk line to afford the target maleimide-terminated PDMAEMA. The formation of maleimide group was confirmed by $^1$H-NMR with the presence of new proton peak at near 6.75.

Conjugation of Albumin to PDMAEMA.

Two stock solutions were made: 1 mM PDMAEMA in PBS (pH7.4, with 20 mM EDTA) buffer and 1 mM BSA in PBS (pH7.4, with 20 mM EDTA) buffer. Two of the solutions were mixed together in different ratio at the ambient temperature. The molar ratios of BSA and PDMAEMA in each mixture were 1:1, 5:1, 10:1, and 20:1, respectively. Each mixture was degassed with nitrogen for 1 h to get rid of oxygen in the solution and then stirred for 18 h to allow the thiol-ene click reaction between the thiol group on the BSA and the maleimide group on the end of the PDMAEMA polymer chain to proceed. The product was purified by dialysis in PBS buffer (pH5). Solvent was changed every 2 hours for 5-6 times. The aim of dialysing the samples was to get rid of EDTA which is toxic to cells and bring the conjugates to pH5. The conjugates of albumin and PDMAEMA with different chain length at a ratio of 2:1 were obtained using the same procedure.

Figure 22:
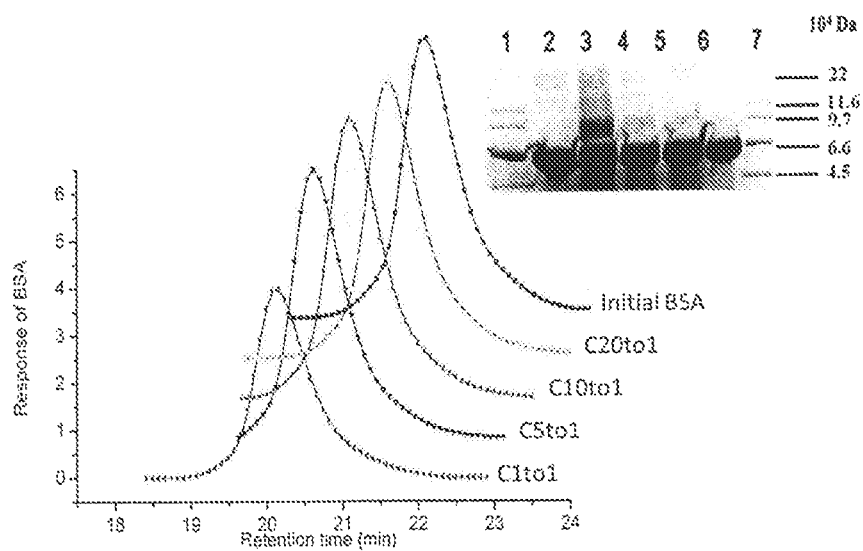
FIG. 22 shows water GPC traces from Example 3 of the initial BSA and the BSA residuals after reaction. The inset is SDS-PAGE (sodium dodecyl sulfate polyacrylamide gel electrophoresis) for the conjugation of BSA and PDMAEMA in different molar ratios. From left to right, Lane 2, BSA; Lane 3, C1to1; Lane 4, C5to1; Lane 5, C10to1; Lane 6, C20to1. In addition, Lane 1 is the standard protein ladders marker.

FIG. 22 shows the conjugation efficiency at different ratios of albumin to polymer.

Formation of Polyion Complex Micelles from Albumin-PDMAEMA Conjugates and ISIS 5132.

Solutions of albumin-PDMAEMA conjugates with required albumin to PDMAEMA ratios were prepared. The resulting conjugates were dialysed in 0.05 M PBS (pH5) for 12 h by changing solvent every 2 h. The solutions of ISIS 5132 in MilliQ water with different concentration were added dropwise to the conjugates solution (pH5) to yield a polyion complex micelle with certain N/P ratios (molar ratio of positive charged nitrogen (polymer) to negatively charged phosphate (oligonucleotide). The complex could be used immediately in pH 5 since the current complex had a tendency to agglomerate. Alternatively, raising the pH value to pH 7 by adding NaOH allowed the formation of solution which was stable over an extended period of time. Given that the cell grows at neutral environment, the latter routine was preferred. Herein, a control experiment was carried out using inactive DNA instead of ISIS 5132. All the conditions were kept consistent to the corresponding oligonucleotide samples. In addition, the oligonucleotide transfection efficiency of the PEGMEMA-PDMAEAM cationic block copolymer was investigated. The same protocol was adopted to make the polyion complex micelles from this polymer solution.

The condensation of the oligonucleotide was therefore carried out when the conjugate solution was at pH5 and the oligonucleotide was dissolved in MilliQ water. The albumin-polymer conjugates with a pH of 5 was then slowly added to the solutions of ISIS 5132 with the concentration of 200 μg/ml (ζ=−29.87 mV at pH7). As shown in Table 5, the resulting polyion complexes have sizes of around 12-15 nm (=−0.41 mV at pH5 and −4.16 mV at pH7) when C1to1 was added to the ISIS 5132 solution (N/P ratio=12). If using the conjugates with higher ratios of BSA to polymer, the particle size of the polyion complex micelle was seen to increase dramatically due to the natural aggregation of albumin. After the complex micelle was stable, the system was brought back to pH7. There are several reasons for this: to reduce the aggregation of the micelle, to protect the oligonucleotide and to keep the neutral environment for cells in the afterward cytotoxicity assays.

TABLE 5

The hydrodynamic diameter and zeta potential of the relevant materials and the complexes

| | Sample name* | $D_h$ (nm) | Zeta potential (mV) |
|---|---|---|---|
| Drug only | ISIS 5132 at pH 7, 200 ug/ml | 0-107 | −29.87 |
| BSA only | BSA at pH 7 conc. of BSA, 1 mg/ml | 5.4 | −5.64 |
| | BSA at Ph 5 conc. of BSA, 1 mg/ml | 6.28 | −2.53 |
| Polymer only | PDMAEMA at pH 7, 0.21 mg/ml | 0 | 7.63 |
| Polymer-BSA conjugate | C1to1 at pH 7 conc. of BSA, 1 mg/ml | 6.16 | 2.04 |
| | C1to1 at pH 5 conc of BSA, 1 mg/ml | 7.43 | 10.87 |
| | C5to1 at pH 7 conc. of BSA, 1 mg/ml | 5.17 | 0.51 |
| | C5to1 at pH 5 conc. of BSA, 1 mg/ml | 6.01 | 3.33 |
| Polymer-BSA conjugate complexed with oligo-nucleotide | C1to1/oligo complex at pH 7 8 h conc. of BSA, 1 mg/ml | 15.8 | −4.16 |
| | C5to1/oligo complex in pH 7 8 h conc. of BSA, 1 mg/ml | 23.9 | −9.07 |
| | C10to1/oligo complex in pH 7 8 h conc. of BSA, 1 mg/ml | ~1000 | −10.8 |
| | C20to1/oligo complex in pH 7 8 h conc. of BSA, 1 mg/ml | ~1000 | −12.4 |

Figure 23:
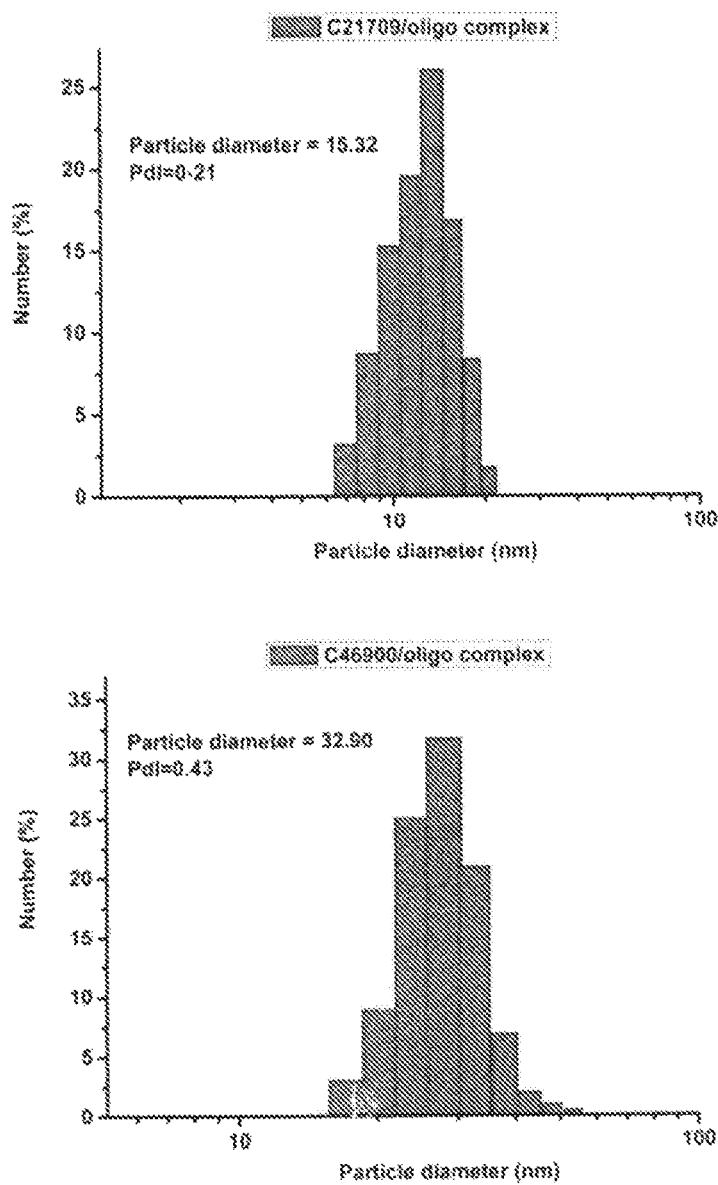
FIG. 23 shows particle size distributions of C21709 (PDMAEMA of MW=21709 g/mol)/oligonucleotide, C46900/oligonucleotide C21709 (PDMAEMA of MW=46900 g/mol) and PEGMEMA-b-PDMAEMA/oligonucleotide at N/P=4 in Example 3 (N/P ratio: molar ratio of nitrogen (polymer) to phosphate (oligonucleotide); PEG-MEMA is polyethylene glycol methyl ether methacrylate).
Figure 24:
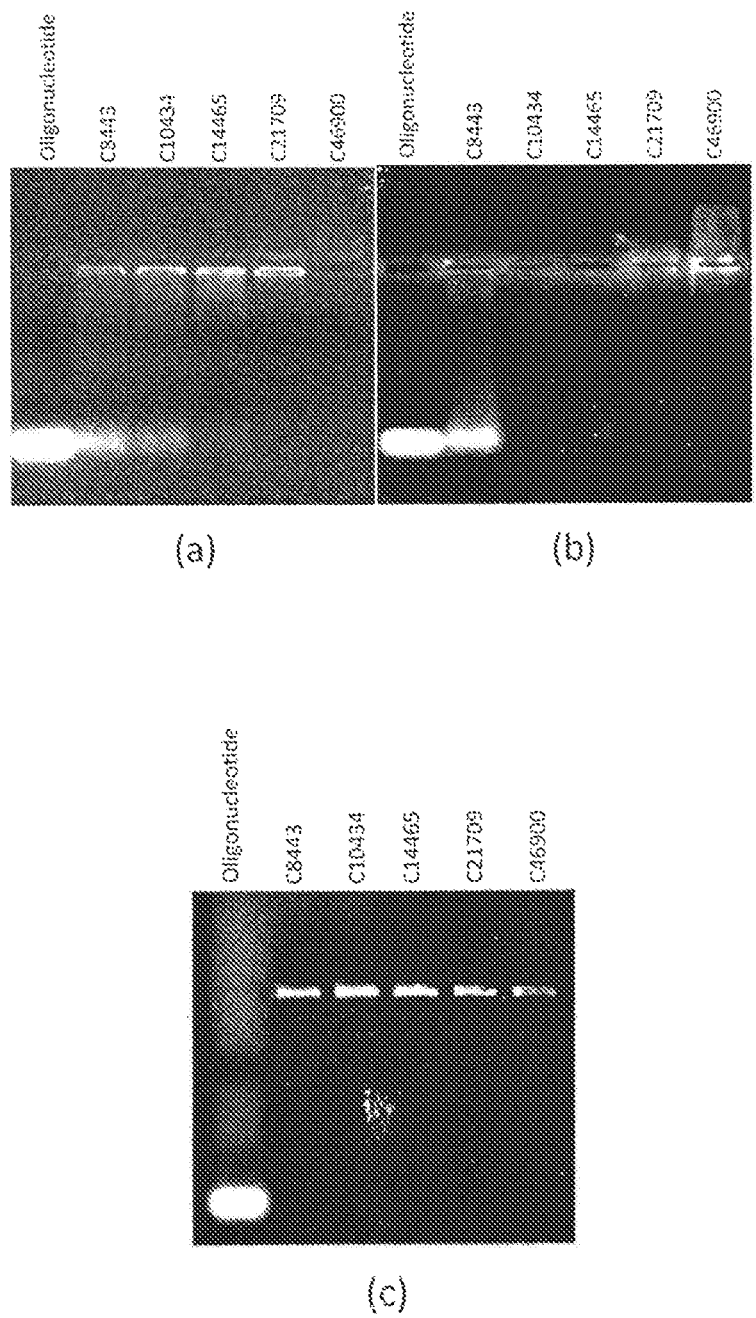
FIG. 24 shows agarose gel shift assays for Example 3 of the BSA-PDMAEMA conjugate (using PDMAEMA molecular weights of 8443 to 46900 g/mol)/Oligonucleotide complex. (a) The shift of the complex after 15 mins (ethidium bromide loaded in running buffer); (b) the shift of the complex after 8 h (ethidium bromide loaded in running buffer); (c) the shift of the complex after 8 h (ethidium bromide complex with oligonucleotide first). In the agarose gel image, Oligonucleotide stands for the initial oligonucleotide and C8443 stands for the free oligonucleotide after binding with the C8443 conjugates, and so on. N/P Ratio: C8443/oligo=2, C10434/oligo=3, C14465/oligo=4, C21709/oligo=6, C46900/oligo=14. (The number after "C" indicates the molecular weight $M_W$ of the polymer in g/mol)

*the sample name C"x" to "y" describes the molar ratio between albumin to PDMAEMA FIG. 23 shows how the particle size may be controlled by controlling the chain length of the polymer used in making the albumin-polymer conjugate. C21709 has a molecular weight of Mn=21709 g/mol; C46900 has a molecular weight of Mn=46900 g/mol. FIG. 24 shows the binding efficiency between conjugates of different molecular weight and the oligonucleotide.

Cell Uptake and Toxicity Testing

Cell Uptake Study Using Laser Scanning Confocal Microscopy.

Human ovarian carcinoma Ovcar-3 cells were seeded in 35 mm Fluorodish (World Precision Instruments) at a density of 60,000 per dish and cultured for 3 days with RPMI 1640 medium supplemented with 10% fetal bovine serum. Micelle solution was loaded to Ovcar-3 cells at a working concentration of 50 μg/mL and incubated at 37° C. for 2 hrs. After incubation, the cells were washed twice with phosphate buffered saline (PBS, pH 7.4). Then the cells were stained with 100 nM LysoTracker Red DND-99 (Invitrogen) for 1 min. The dye solution was quickly removed and the cells were gently washed with PBS. Finally, the cells were mounted in PBS and observed under a laser scanning confocal microscope system (Zeiss LSM 780). The system was equipped with a Diode 405-30 laser, an argon laser and a DPSS 561-10 laser (excitation and absorbance wavelengths: 405 nm, 488 nm and 561 nm, respectively) connected to a Zeiss Axio Observer. Z1 inverted microscope (oil immersion×100/1.4 NA objective). The ZEN2011 imaging software (Zeiss) was used for image acquisition and processing.

Cytotoxicity Testing.

Human Ovarian Carcinoma Ovcar-3 cells and Chinese Hammer Ovarian (CHO) cells were cultured in tissue culture flasks with Medium RPMI1640 supplemented with 10% foetal bovine serum at 37° C. under a 5% $CO_2$ atmosphere. After reaching confluency, cells were collected from the flasks with Trypsin/EDTA treatment. The cell suspension was then seeded into a 96-well cell culture plate at a cell density of 40,000 cells·$mL^{-1}$, 200 μL·$well^{-1}$. After incubation for one day, the cell in the plate was subsequently used for cytotoxicity testing. This involved firstly sterilising the micelles by UV irradiation for 1 hour, and serially diluting by half the solution with sterile water. The medium in the cell culture plate was discarded and replaced with 100 μL, of fresh twice-concentrated RPMI1640 medium and the cells were incubated with the micelles for 48 hours. The cell viability was then investigated first by addition of cold TCA. The culture medium was discarded and 100 μL of 10% TCA was added to each well, followed by incubation of the plates for 30 min at 4° C. The supernatant was discarded and the plates washed 5 times with water and air-dried. 100 μL of SRB (sulphorhodamin B) solution 0.4% (w/v) in 1% acetic acid was added to each well, and the plates incubated for 15 minutes at room temperature. After staining, the unbound dye was removed by washing 5 times with 1% acetic acid and the plates air-dried. Bound stains were solubilised with 200 μL 10 mM Tris Buffer and absorbance was measured on a Bio-Rad BenchMark® microplate reader (λ=490 nm), with data analysed and plotted using GraphPad Prism 6.0, as shown in FIG. 25.

Figure 25:
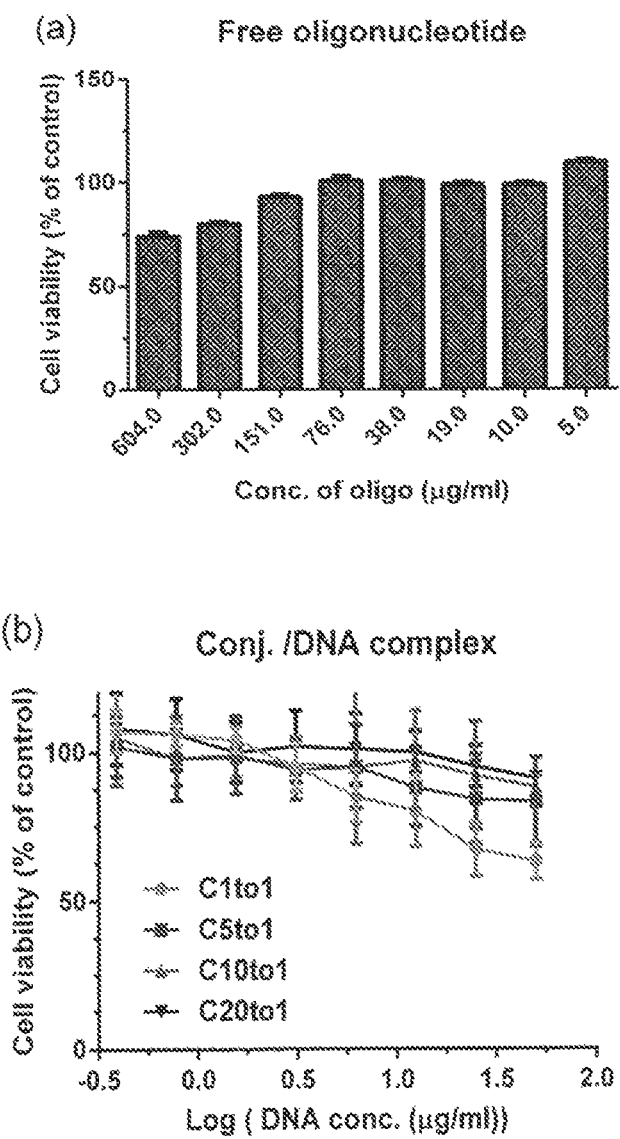
FIG. 25 shows cytotoxicity assays of free oligonucleotide (a), albumin-polymer conjugates/DNA complex micelle (control) (b), and albumin-polymer conjugates/oligonucleotide complex micelle against Ovcar-3 ovarian cancer cells for 48 h (c).
Figure 25:
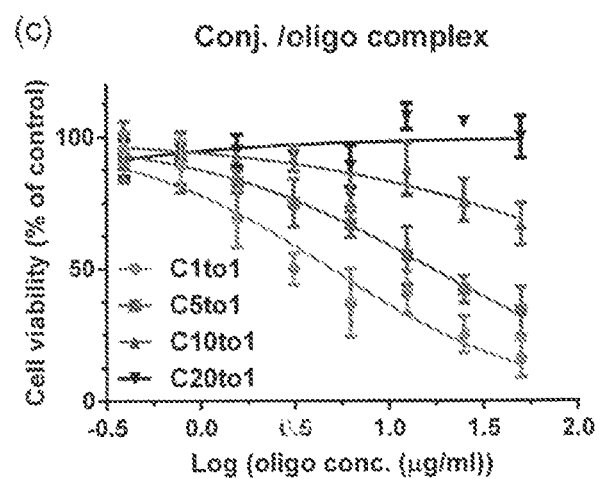
Figure 26:
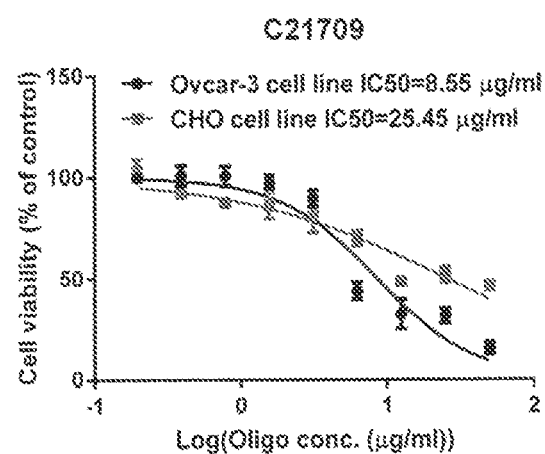
FIG. 26 shows cytotoxicity assays of C21709/Oligo complex micelle, and C46900/Oligo complex micelle, against Ovcar-3 ovarian cancer cells and healthy ovarian CHO (Chinese Hamster Ovary) cells for 48 h.
Figure 26:
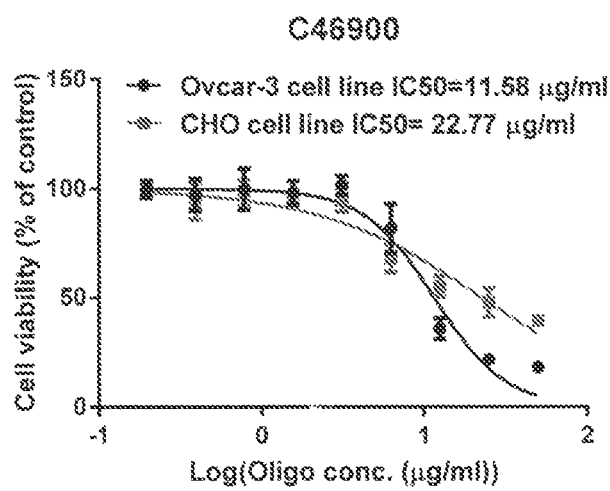

FIG. 25 shows the effect of the albumin/polymer ratio on delivery and toxicity of the oligonucleotide incorporated into the micelles. FIG. 26 shows the effect of polymer molecular weight on delivery and toxicity of the oligonucleotide incorporated into the micelles.

In summary, albumin based micelles have been shown to enable the transport of oligonucleotides into tumour cells where a drug is released from the micelles resulting in cell death. The activity of the oligonucleotide is influenced by the molecular weight of the cationic polymer.

Example 4

Figure 27:
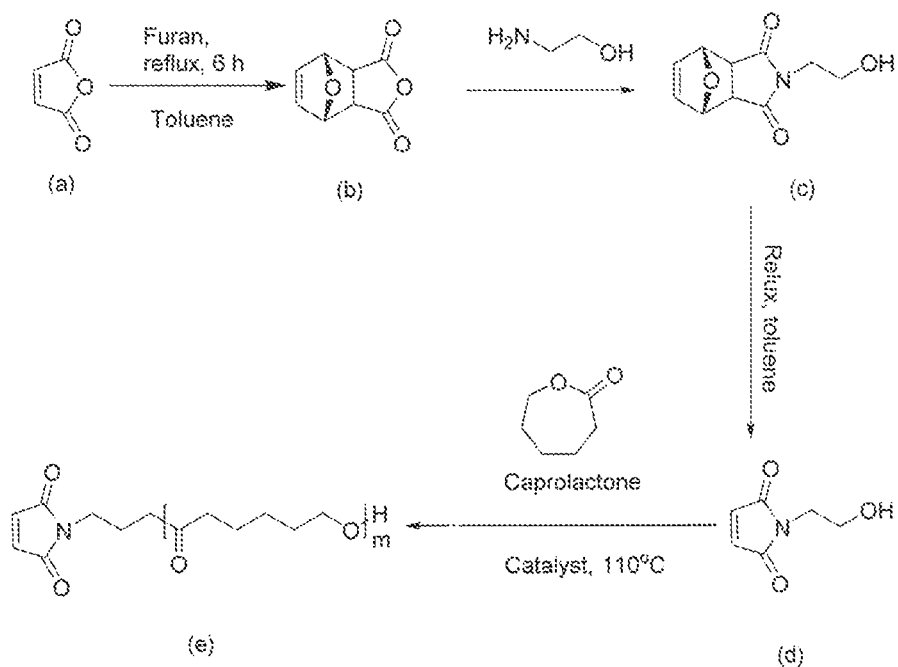
FIG. 27 shows a scheme of the synthesis of maleimide-terminated polycaprolactone (PCL) from Example 4.

This example demonstrates the preparation of a fully degradable albumin micelle based on a polyester conjugated to albumin. FIG. 27 shows the synthesis of maleimide-terminated polycaprolactone. This polymer was then conjugated to BSA and the resulting micelles were loaded with curcumin. The product was tested for particle size and cytotoxicity against prostate cancer.

Figure 28:
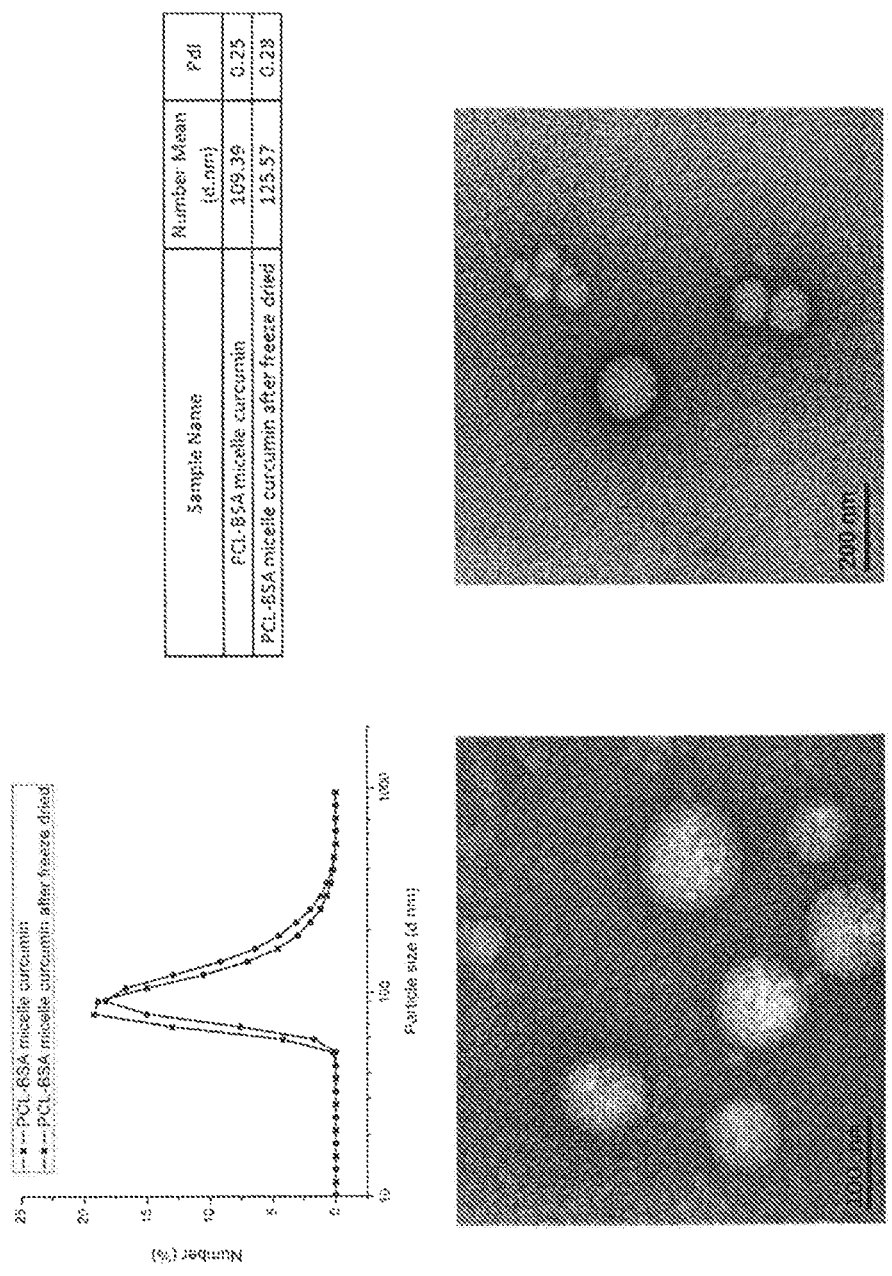
FIG. 28 shows size analysis of PCL-BSA micelles loaded with curcumin from Example 4. Top: DLS analysis of the particle directly after synthesis and after freeze-drying and re-dissolving in water. Bottom left: TEM analysis of the solution directly after loading the particles with curcumine; bottom right: TEM analysis after freeze-drying and re-dissolving
Figure 29:
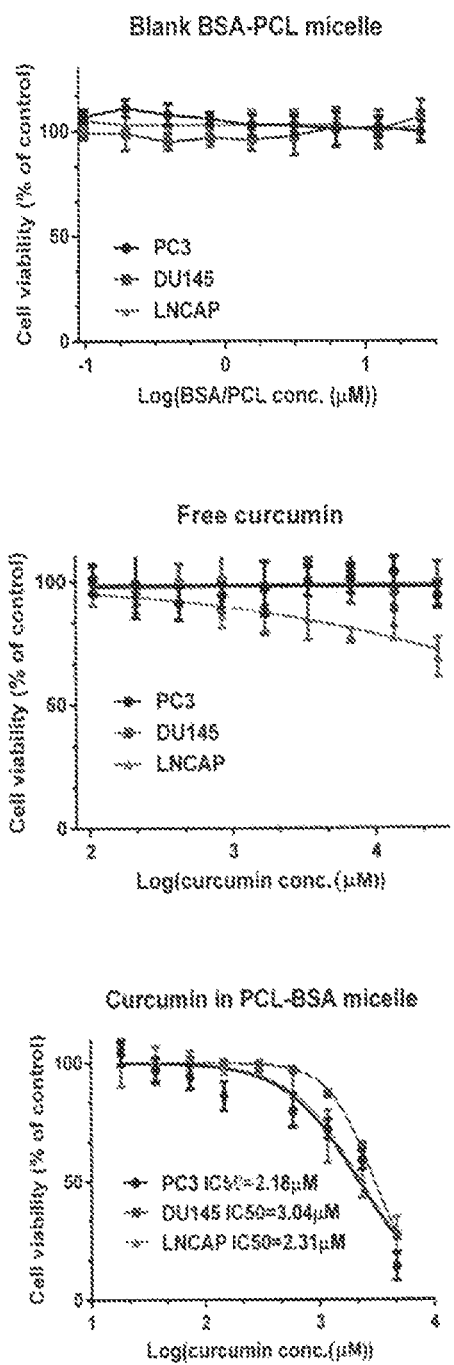
FIG. 29 shows cytotoxicity results from Example 4 against three prostate cancer cell lines: Top: the empty micelles were non-toxic; middle: curcumin showed only negligible toxicity in the chosen concentration range; bottom: toxicities of curcumin loaded albumin-micelles
Figure 30:
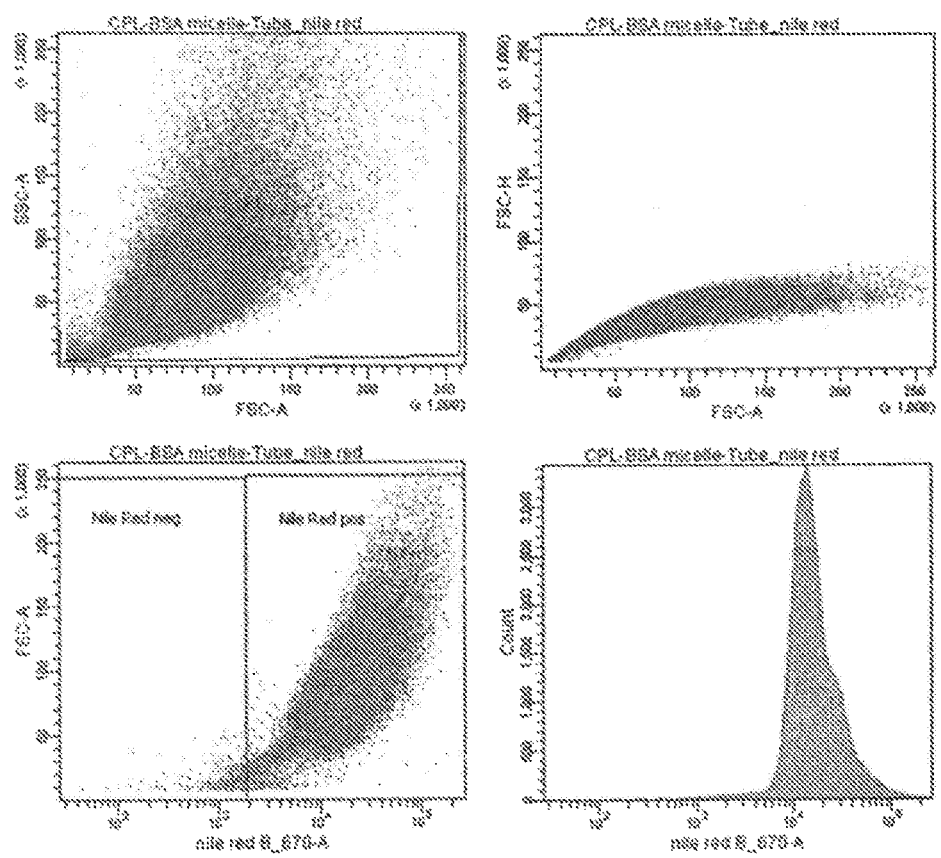
FIG. 30 shows flow cytometry analysis from Example 4, showing the efficient uptake of BSA micelles by prostate cancer cells.

FIG. 28 shows size analyses of the micelles, FIG. 29 shows their cytotoxicity and FIG. 30 illustrates the uptake of the micelles by prostate cancer cells.

This experiment demonstrates the enhanced delivery of curcumin using albumin based micelles. The IC50 value was improved by a factor of more than 10 since the drug was efficiently taken up via the drug carrier. The albumin micelle is now fully degradable and can potentially be fully removed from the body

The invention claimed is:

1. A substance comprising a plurality of assemblies, each of said assemblies comprising a plurality of albumin derivatives and a drug, each albumin derivative comprising an albumin having a polymer chain coupled thereto, wherein the polymer chain is coupled to a single site of the albumin, wherein the assemblies comprise a core comprising the polymer chains of the albumin derivatives and a shell comprising the albumin of the albumin derivatives, wherein the drug is located at least partially in the core of the assemblies, wherein the albumin having the polymer chain coupled thereto of the albumin derivatives is undenatured, wherein the polymer chain is selected from a hydrophobic polymer chain and an ionically charged polymer chain, and wherein when the polymer chain is a hydrophobic polymer chain, the drug is hydrophobic, and when the polymer chain is an ionically charged polymer chain, the drug is a counterion to the ionically charged polymer chain.

2. The substance of claim 1 which is in the form of a powder.

3. The substance of claim 1 which has a water content of less than 2% on a weight basis based on the total weight of the substance.

4. A pharmaceutical composition comprising the substance of claim 1 together with one or more pharmaceutically acceptable carriers, diluents and/or adjuvants.

5. The pharmaceutical composition of claim 4 which is in the form of a powder.

6. The pharmaceutical composition of claim 5 which has a water content of less than 2% on a weight basis based on the total weight of the substance.

7. The substance of claim 1, wherein the thio group is on a cysteine residue.

8. The substance of claim 7, wherein the thio group is on a cysteine residue.

9. The substance of claim 1, wherein the polymer chain has a polydispersity index of about 1.2 to about 2.

10. The substance of claim 1, wherein each of said assemblies consist of a plurality of the albumin derivatives and the drug.

11. A process for making a substance according to claim 1 comprising:
Providing a dispersion of assemblies, said assemblies comprising an albumin derivative comprising albumin having a polymer chain coupled thereto, wherein the assemblies comprise a core comprising the polymer chains and a shell comprising the albumin; and
Drying said dispersion, thereby making the substance according to claim 1.

12. The process of claim 11 wherein the step of drying comprises freeze-drying.

13. The process of claim 11 wherein the drying is conducted to a water content of less than about 2% by weight.

14. A process for making a dispersion of assemblies, said assemblies comprising an albumin derivative comprising albumin having a polymer chain coupled thereto, wherein the assemblies comprise a core comprising the polymer chains and a shell comprising the albumin comprising:
Providing a substance according to claim 1; and
Combining said substance with water or an aqueous solution, thereby making a dispersion of assemblies, said assemblies comprising an albumin derivative comprising albumin having a polymer chain coupled thereto, wherein the assemblies comprise a core comprising the polymer chains and a shell comprising the albumin.

15. The process of claim 14 additionally comprising agitating the substance in the aqueous solution so as to disperse the substance in the aqueous solution.

* * * * *